US009271936B2

(12) United States Patent
DeShong et al.

(10) Patent No.: US 9,271,936 B2
(45) Date of Patent: Mar. 1, 2016

(54) METHOD FOR FORMING MESOPOROUS SILICA NANOPARTICLES, MESOPOROUS SILICA NANOPARTICLES, AND APPLICATIONS THEREOF

(75) Inventors: Philip R. DeShong, Silver Spring, MD (US); Michael R. Zachariah, Potomac, MD (US); Peter DeMuth, Towson, MD (US); Anand Prakash, Wilmington, MA (US); Charles Luckett, Greenbelt, MD (US); Douglas Stephen English, Wichita, KS (US)

(73) Assignee: UNIVERSITY OF MARYLAND, College Park, MD (US)

( * ) Notice: Subject to any disclaimer, the term of this patent is extended or adjusted under 35 U.S.C. 154(b) by 1223 days.

(21) Appl. No.: 12/382,041

(22) Filed: Mar. 6, 2009

(65) Prior Publication Data

US 2009/0311332 A1 Dec. 17, 2009

Related U.S. Application Data

(60) Provisional application No. 61/034,269, filed on Mar. 6, 2008, provisional application No. 61/034,271, filed on Mar. 6, 2008.

(51) Int. Cl.
*A61K 9/14* (2006.01)
*A61K 31/704* (2006.01)
*A61K 47/48* (2006.01)
*B82Y 5/00* (2011.01)

(52) U.S. Cl.
CPC .............. *A61K 9/143* (2013.01); *A61K 31/704* (2013.01); *A61K 47/48861* (2013.01); *B82Y 5/00* (2013.01); *Y10S 977/773* (2013.01); *Y10S 977/906* (2013.01); *Y10S 977/911* (2013.01); *Y10S 977/927* (2013.01)

(58) Field of Classification Search
None
See application file for complete search history.

(56) References Cited

U.S. PATENT DOCUMENTS

| 2002/0127498 A1* | 9/2002 | Doshi et al. | 430/322 |
| 2004/0005351 A1* | 1/2004 | Kwon et al. | 424/450 |
| 2010/0255103 A1* | 10/2010 | Liong et al. | 424/489 |

OTHER PUBLICATIONS

G-R Yi, S-M Yang. "Microstructures of Porous Silica Prepared in Aqueous and Nonaqueous Emulsion Templates." Chem. Mater., vol. 11, 1999, pp. 2322-2325.*

J-F Chen, H-M Ding, J-X Wang, L Shao. "Preparation and characterization of porous hollow silica nanoparticles for drug delivery application." Biomaterials, vol. 25, 2004, pp. 723-727.*

* cited by examiner

*Primary Examiner* — Isaac Shomer
(74) *Attorney, Agent, or Firm* — Squire Patton Boggs (US) LLP

(57) ABSTRACT

A method for synthesizing a mesoporous silica nanoparticle, a mesoporous silica nanoparticle, and applications thereof are provided. The method includes fractionating a mesoporous silica nanoparticle suspension to produce size-fractionated mesoporous silica nanoparticle. The method further includes etching the size-fractionated mesoporous silica nanoparticle to produce synthesized mesoporous silica nanoparticle having a hollow, porous morphology configured to receive one of a therapeutic agent and an imaging material. The etching includes differential etching of silica from areas of low polymeric density within the mesoporous silica nanoparticle and re-depositing of the silica in areas of higher polymeric density existing near the surface of the mesoporous silica nanoparticle. A target material is loaded into the synthesized mesoporous silica nanoparticle and a controlled released of the target material is provided by decreasing the physiological pH of the surface of the mesoporous silica nanoparticle.

11 Claims, 27 Drawing Sheets

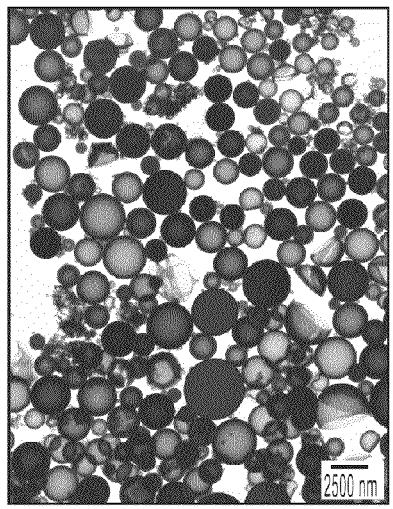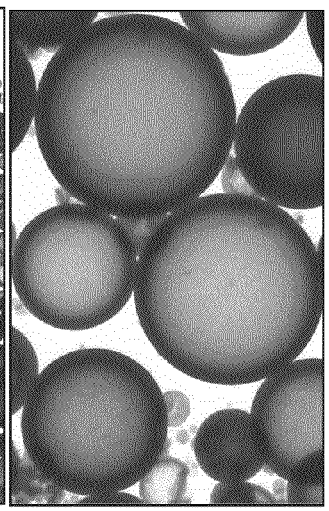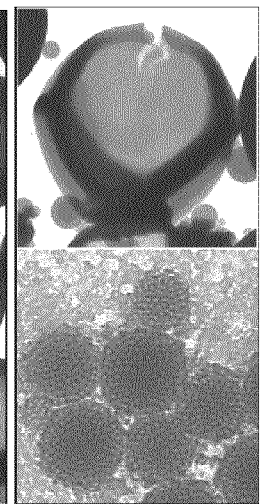
FIG.4a      FIG.4b      FIG.4c
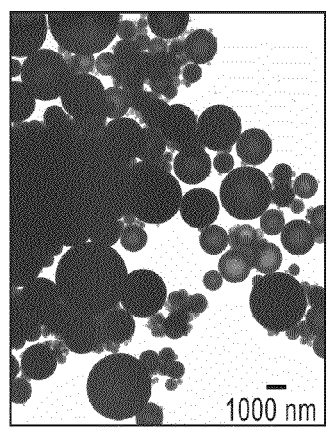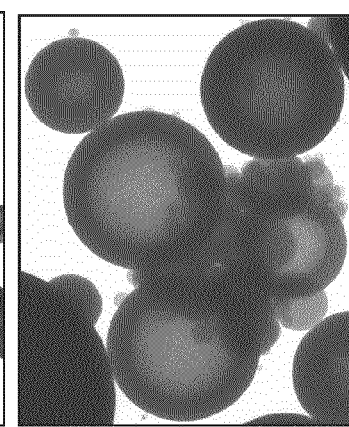
FIG.5a      FIG.5b

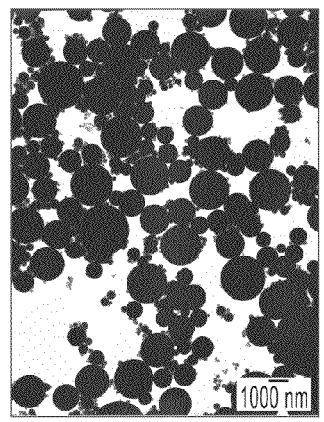 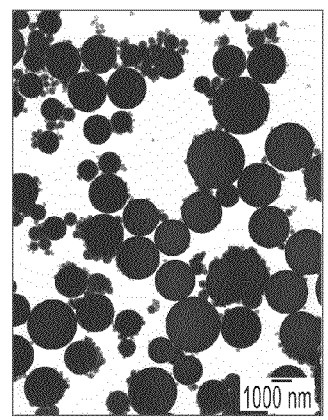 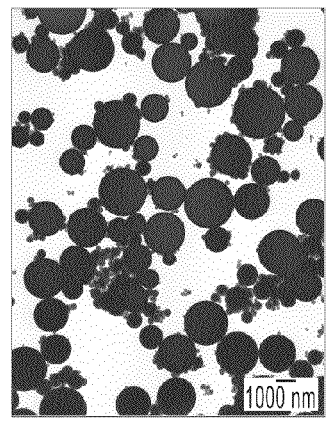
FIG.10a  FIG.10b  FIG.10c
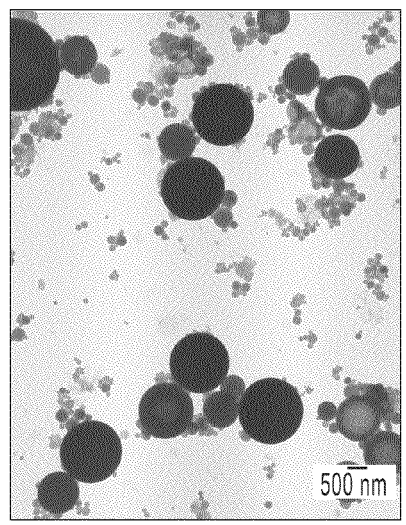 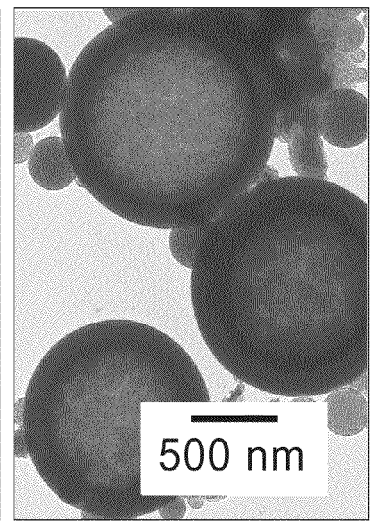
FIG.11a  FIG.11b

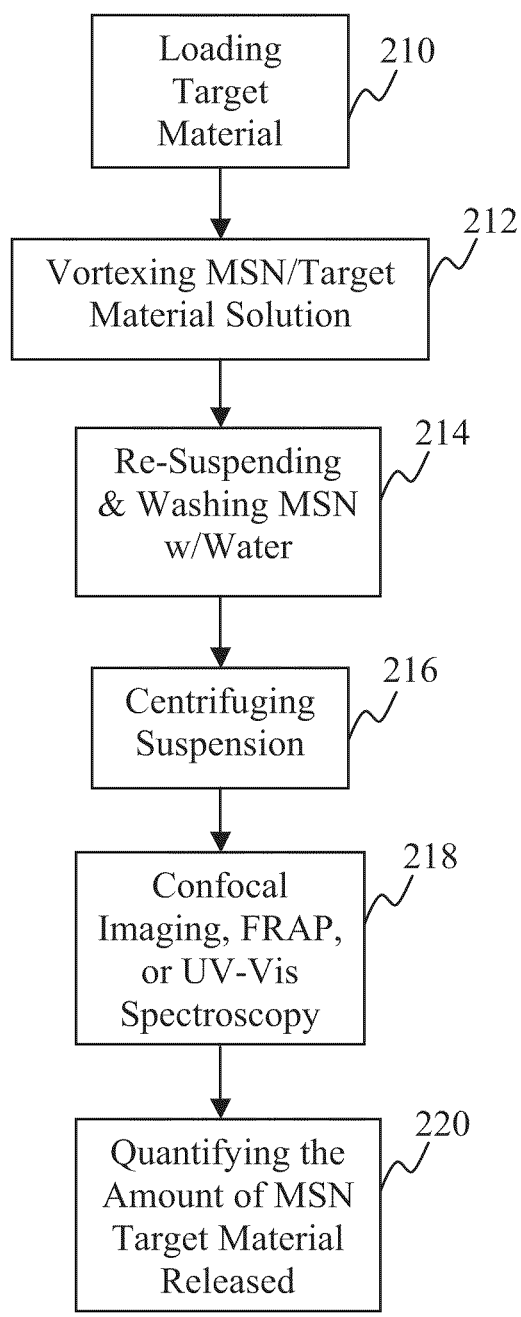

METHOD FOR FORMING MESOPOROUS SILICA NANOPARTICLES, MESOPOROUS SILICA NANOPARTICLES, AND APPLICATIONS THEREOF

CROSS REFERENCE TO RELATED APPLICATIONS

This application claims priority under 35 U.S.C. §119(e) of U.S. Provisional Patent Application Ser. No. 61/034,269, filed on Mar. 6, 2008, and U.S. Provisional Patent Application Ser. No. 61/034,271, filed on Mar. 6, 2008. The subject matter of the earlier filed applications are hereby incorporated by reference.

This invention was made with United States Government support under Contract No. CTS0608906 awarded by the National Science Foundation. The United States Government has certain rights in this invention.

BACKGROUND

1. Field

The invention relates to a method for synthesizing mesoporous silica nanoparticles. More particularly, the invention relates to a method for synthesizing mesoporous silica nanoparticles of a defined size with a controlled porosity and pore size. The invention also relates to the loading and releasing of target materials from the synthesized mesoporous silica nanoparticles, and the functionalization of the synthesized mesoporous silica nanoparticles with biologically relevant glycoconjugates allowed for specific cellular targeting, demonstrating the applicability of the mesoporous silica nanoparticles for both specific cellular imaging and diagnostics, and targeted drug delivery.

2. Description of the Related Art

A current problem with chemotherapy is that cancer treatment drugs are not specific in treatment. Essentially, cancer treatment drugs are designed to disable processes that occur more frequently in cancer tissue than in healthy tissue. However, this approach is severely limited because although cancer cells are preferentially affected, healthy tissue may still be damaged to a significant extent based on the strength of the drug treatment. Therefore, in traditional chemotherapy, the strength of cancer treatment drugs that can be used is limited by the adverse effects to healthy tissue necessary for sustaining life.

Traditionally, cancer treatment drugs have achieved improved selectivity through mode of action, however, better processes are needed to minimize the damage to healthy tissue.

Current research directives in targeted drug delivery, specific cellular imaging, and diagnostics provide solutions to these problems, and will undoubtedly constitute the basis for chemotherapy in the future. For example, the use of bio-functionalized nano-materials for targeted drug delivery may allow for unprecedented specificity in the targeting of drugs on cancer cells with minimal collateral damage to healthy tissue. Similar bio-functionalization targeting techniques may also allow for more precise and sensitive diagnostic imaging, providing for early detection and diagnosis of cancer tissue, thereby leading to a more effective treatment of cancer.

Mesoporous silica nanoparticles (MSN) have been shown to possess characteristics indicating their potential utility for applications in medical and biotechnical applications, such as drug delivery, medical diagnostic cell imaging, and bio-systems analysis.

Accordingly, what is needed is a method for synthesizing a MSN of a defined size with a controlled porosity and pore size, whereby a surface charge on the MSN can be easily manipulated via post-synthetic modifications for controlling the release of a drug or fluorescent absorbed in the MSN only after the drug or fluorescent has been endocytosed into a target tissue.

SUMMARY

In accordance with an embodiment of the invention, there is provided a method for synthesizing a mesoporous silica nanoparticle. The method includes fractionating mesoporous silica nanoparticle suspensions to produce a size-fractionated mesoporous silica nanoparticle. The method further includes differential etching of silica from areas of low polymeric density within the size-fractionated mesoporous silica nanoparticle. Further, the method includes re-depositing the silica in areas of higher polymeric density existing near the surface of the size-fractionated mesoporous silica nanoparticle to produce synthesized mesoporous silica nanoparticle including a hollow, porous morphology configured to receive one of a therapeutic agent and an imaging material.

In accordance with another embodiment of the invention, there is provided a method for loading and releasing a target material from a mesoporous silica nanoparticle. The method includes loading a target material into mesoporous silica nanoparticle. The target material includes one of a therapeutic agent and an imaging material. The method further includes releasing the target material from the mesoporous silica nanoparticle by decreasing the surface pH of the mesoporous silica nanoparticle to physiologically stimulate a release mechanism in the mesoporous silica nanoparticle.

In accordance with another embodiment of the invention, there is provided a mesoporous silica nanoparticle. The mesoporous silica nanoparticle includes a target material. The target material includes one of a therapeutic agent and an imaging agent. The mesoporous silica nanoparticle also include a mannose bioconjugate configured to enhance the release of the target material from the mesoporous silica nanoparticle. The mesoporous silica nanoparticle is configured to release the target material by decreasing the surface pH of the mesoporous silica nanoparticle to physiologically stimulate a release mechanism in the mesoporous silica nanoparticle.

In accordance with another embodiment of the invention, there is provided a method for cancer treatment drug delivery. The method includes synthesizing a mesoporous silica nanoparticle, and loading a target material into the mesoporous silica nanoparticle. The target material includes one of a therapeutic agent and an imaging material. The method further includes functionalizing the target material-loaded mesoporous silica nanoparticle, and applying the functionalized mesoporous silica nanoparticle to cancer tissue. Further, the method includes releasing the target material from the functionalized mesoporous silica nanoparticle to deliver a cancer treatment drug.

BRIEF DESCRIPTION OF THE DRAWINGS

Further aspects, details, advantages and modifications of the invention will become apparent from the following detailed description of the preferred embodiments which is to be taken in conjunction with the accompanying drawings, in which:

FIG. 4a shows a causation in morphology development for hollow MSN developed through sequential centrifugal filtration, in accordance with an embodiment of the invention.

FIG. 4b shows cracked MSN observed after centrifugal filtration, providing evidence of mechanical stress produced by sequential centrifugal filtration, in accordance with an embodiment of the invention.

FIG. 4c shows small silica particle formation observed after MSN timed exposure to water, providing evidence of water based etching, in accordance with an embodiment of the invention.

FIGS. 5a and 5b show TEM images of hollow morphology development of MSN after four centrifugal filtration sequences.

FIGS. 10a, 10b, and 10c show TEM images of MSN in a water suspension for two days, four days, and eleven days, respectively, in accordance with an embodiment of the invention.

FIGS. 11a and 11b show TEM images of hollow particles synthesized using BOE silica etching for 30 minutes, in accordance with an embodiment of the invention.

FIG. 12 is a schematic diagram of a method for loading and releasing a target material from mesoporous silica nanoparticles, in accordance with an embodiment of the invention.

DETAILED DESCRIPTION OF THE PREFERRED EMBODIMENTS

Reference will now be made in detail to the preferred embodiments of the invention, examples of which are illustrated in the accompanying drawings.

In describing certain embodiments of the invention, specific terminology is used for the sake of clarity. However, the invention is not intended to be limited to the specific terminology so selected. A person of ordinary skill in the relevant art will recognize that other equivalent components may be employed and other methods developed without parting from the spirit or the scope of the invention. All references cited herein are incorporated by reference as if each had been individually incorporated.

An embodiment of the invention provides a method for synthesizing MSN having a hollow, porous particle morphology using chemical etching and mechanical stress induced mechanisms. Furthermore, another embodiment of the invention provide a method for loading both therapeutic agents and imaging materials into MSN using one of confocal microscopy, fluorescence recovery after photo-bleaching (FRAP), and ultraviolet-visible (UV-Vis) spectroscopy. Another embodiment of the invention further provides for releasing target materials from MSN under various physiologically relevant pH and ionic strength conditions using UV-Vis spectroscopy. These embodiments exhibit several non-obvious advantages over conventional methods, for example, general and modular functionalization of MSN, controllable pore size and porosity of MSN, and higher fluorescence emission.

An embodiment of the invention provides a method for synthesizing MSN having a hollow, porous particle morphology using buffered oxide etchant (BOE) etching techniques. The method may include differential etching and re-deposition of silica from areas of low polymeric density within the MSN to areas of higher polymeric density observed to exist near the surface of the MSN.

Figure 1A:
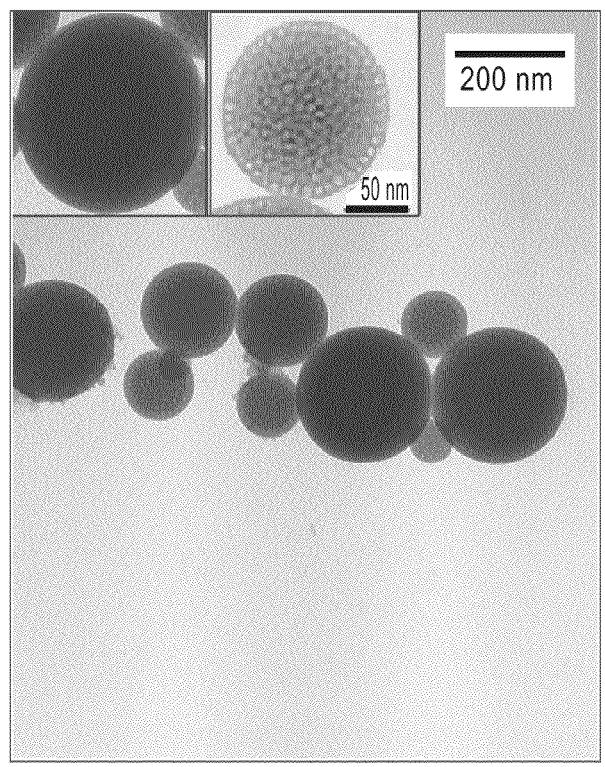
FIG. 1a is a TEM image of solid stock MSN, in accordance with an embodiment of the invention.
Figure 1B:
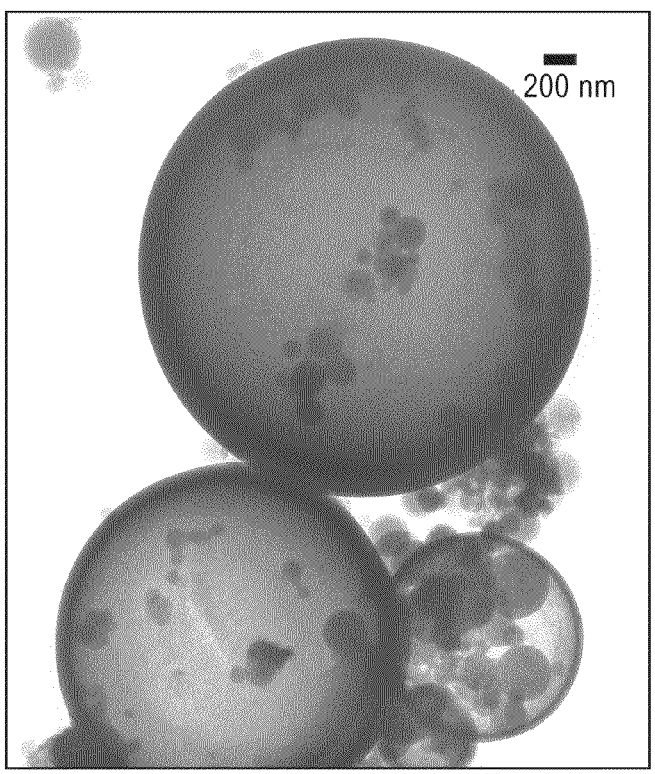
FIG. 1b is an inset of FIG. 1a showing solid and porous particle morphology of hollow MSN after 30 minutes BOE exposure, in accordance with an embodiment of the invention.

FIGS. 1a and 1b illustrate MSN produced by this synthesis method. FIG. 1a is a transmission electron microscopy image of solid stock MSN, in accordance with an embodiment of the invention. FIG. 1b is an inset of FIG. 1a showing hollow MSN with solid and porous particle morphology after 30 minutes of BOE exposure, in accordance with an embodiment of the invention.

Figure 2:
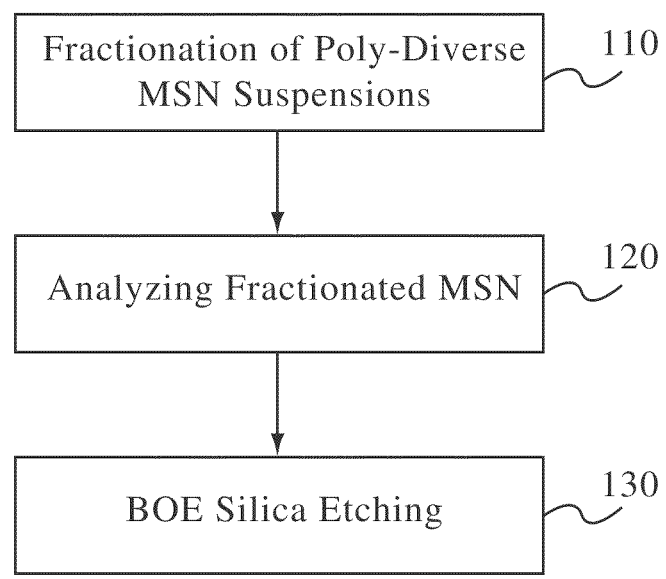
FIG. 2 is schematic diagram of a method for synthesizing MSN as illustrated in FIGS. 1a and 1b, in accordance with an embodiment of the invention.

FIG. 2 is a schematic diagram of a method for synthesizing MSN as illustrated in FIGS. 1a and 1b, in accordance with an embodiment of the invention. The method may include a fractionation of poly-diverse MSN suspensions using one of sequential filtration using graded filters and gravity filtration (step 110). The method may further include analyzing the size of the fractionated MSN using one of dynamic light scattering (DLS) and transmission electron microscopy (TEM) following each filtration (step 120). Further, the method may include a time-dependent water-based differential etching and re-deposition of the silica matrix from which particles are synthesized, for example, buffered oxide etchant (BOE) silica etching (step 130) of the MSN.

Figure 3:
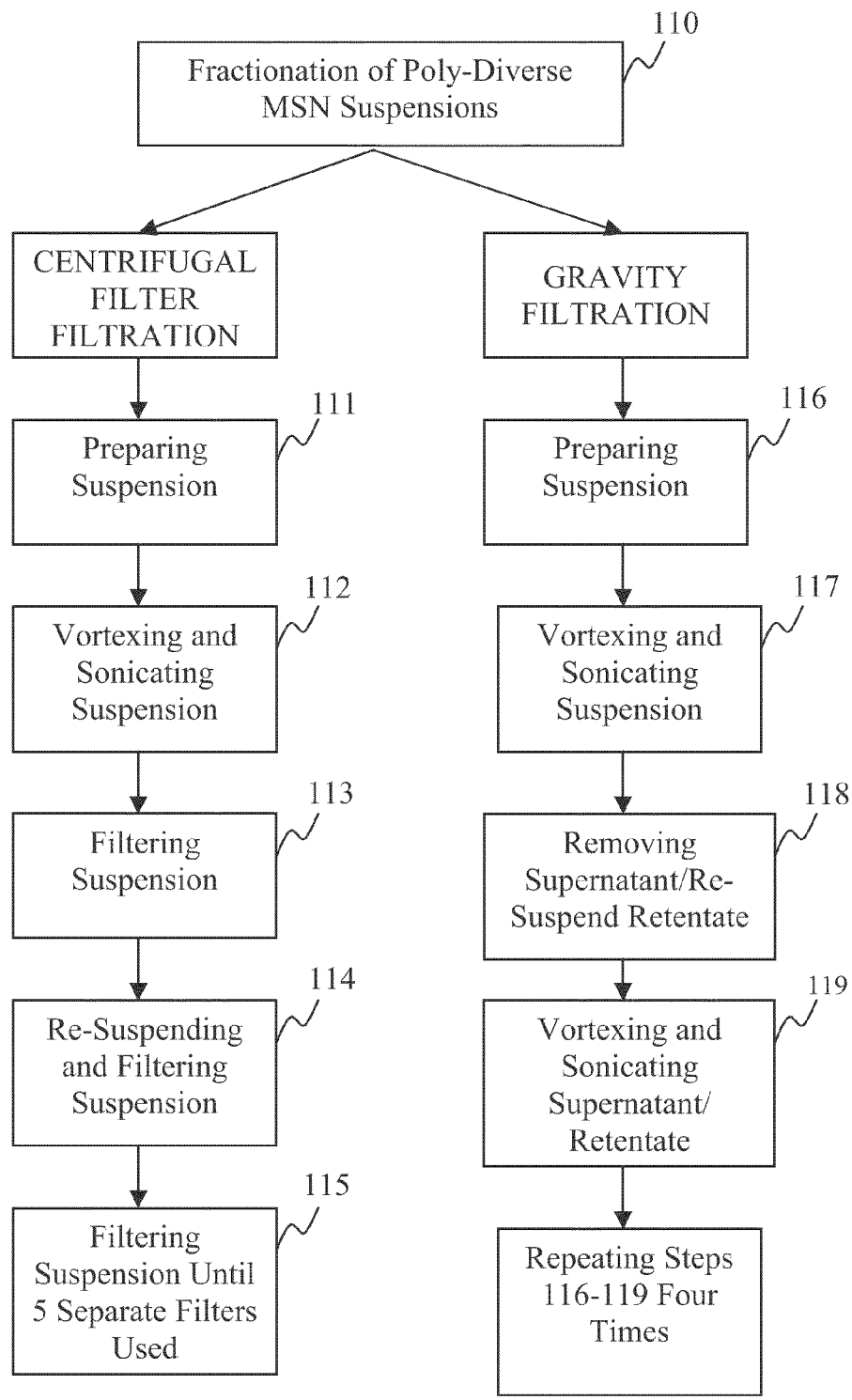
FIG. 3 is a schematic diagram of the fractionation step of the method for synthesizing MSN, in accordance with an embodiment of the invention.

FIG. 3 is a schematic diagram of the fractionation step of the method for synthesizing MSN, in accordance with an embodiment of the invention. As illustrated in FIG. 3, the fractionation of MSN may be accomplished using centrifugal filter fractionation, or sequential centrifugal filtration. Sequential centrifugal filtration may introduce a mechanical stress in the development of the hollow, porous MSN, as illustrated in FIGS. 4a, 4b, and 4c. FIG. 4a shows a causation in morphology development for hollow MSN developed through sequential centrifugal filtration, in accordance with an embodiment of the invention. FIG. 4b shows cracked MSN observed after centrifugal filtration, providing evidence of mechanical stress produced by sequential centrifugal filtration, in accordance with an embodiment of the invention. FIG. 4c shows small silica particle formation observed after MSN timed exposure to water, providing evidence of water based etching, in accordance with an embodiment of the invention.

Hence, FIGS. 4a, 4b, 4c each demonstrate that MSN may be subjected to large mechanical stresses during the filtration process, influencing the breakdown of the polymeric matrix within the MSN, and thus further influencing the development of the hollow particle morphology observed in the fractionated MSN.

Accordingly, as illustrated in FIG. 3, the centrifugal filter fractionation may include preparing a 5 mg/mL stock suspension of MSN in water (step 111). The water may include Millipore water, for example, 18 MΩ water. The suspension may be vortexed for about 20 seconds and subsequently sonicated for 30 minutes, for example, sonicating the vortexed suspension using a Bransonic 321 desk sonicator (step 112). The fractionation further may include filtering a 2 mL aliquot of the suspension using a filter, for example, a 5.0 µm Ultrafree-CL centrifugal filter (step 113). Next, the fractionation may include re-suspending the retentate using 2 mL of water and filtering again using the same filter, for example, the same 5.0 µm Ultrafree-CL centrifugal filter (step 114).

After three successive filtrations using the same filter, the retentate may be filtered using a new filter, for example, a new 5.0 µm Ultrafree-CL centrifugal filter. This process may be repeated until the particles have been filtered using five separate filters, for example, five separate 5.0 µm Ultrafree-CL centrifugal filters (step 115). FIGS. 5a and 5b show TEM images of hollow morphology development of MSN after four centrifugal filtration sequences.

The retentate collected after the final filtration represents the >5.0 µm fraction. Filtrate obtained from the preceding filtrations may be collected and filtered using the steps previously described above, however, the filtrate may be filtered using a 0.65 Ultrafree-CL centrifugal filter. The retentate collected after the final filtration using five separate 0.65 Ultrafree-CL centrifugal filters represents the >5.0-0.65 µm fraction.

As further illustrated in FIG. 3, the fractionation of MSN may also be accomplished using gravity filtration. Gravity filtration may include preparing a 2.0 mg/mL stock suspension of MSN in water (step 116). The water may include Millipore water, for example, 18 MΩ water. The suspension may be vortexed for about 20 seconds and subsequently sonicated for 30 minutes, for example, sonicating the vortexed suspension using a Bransonic 321 desk sonicator (step 117). Supernatant may be removed and a volume of water equal to the volume of supernatant may be used to re-suspend the retentate (step 118). Both the removed supernatant and the re-suspended retentate may be vortexed and subsequently sonicated for 15 minutes (step 119). This procedure may be repeated four times.

Figure 6:
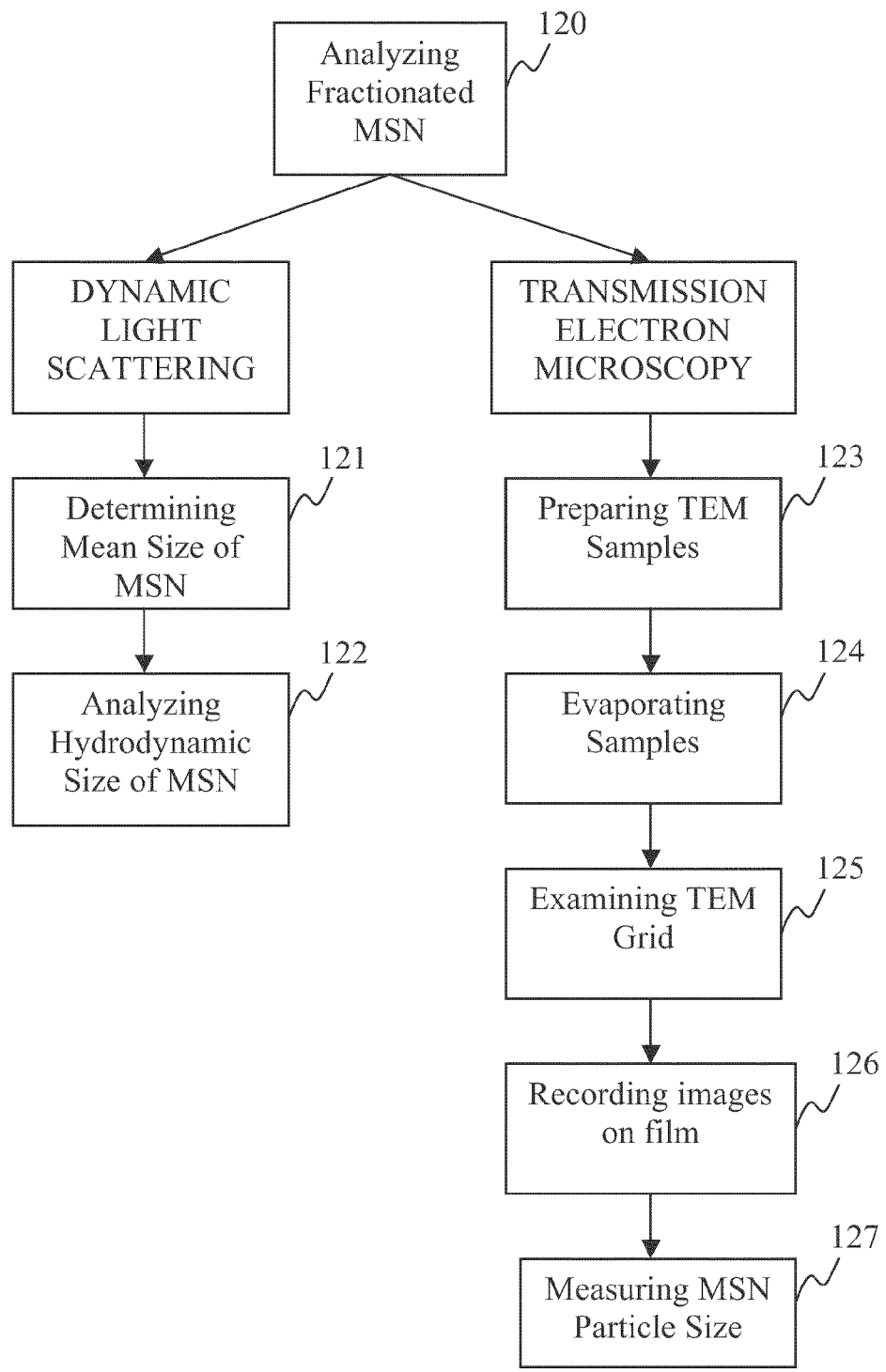
FIG. 6 is a schematic diagram of the analyzing step of the method for synthesizing MSN, in accordance with an embodiment of the invention.

As illustrated in FIGS. 2 and 6, fractionation may further include analyzing the size of the fractionated MSN using one of dynamic light scattering (DLS) and transmission electron microscopy (TEM) following each filtration (step 120).

Figure 7A:
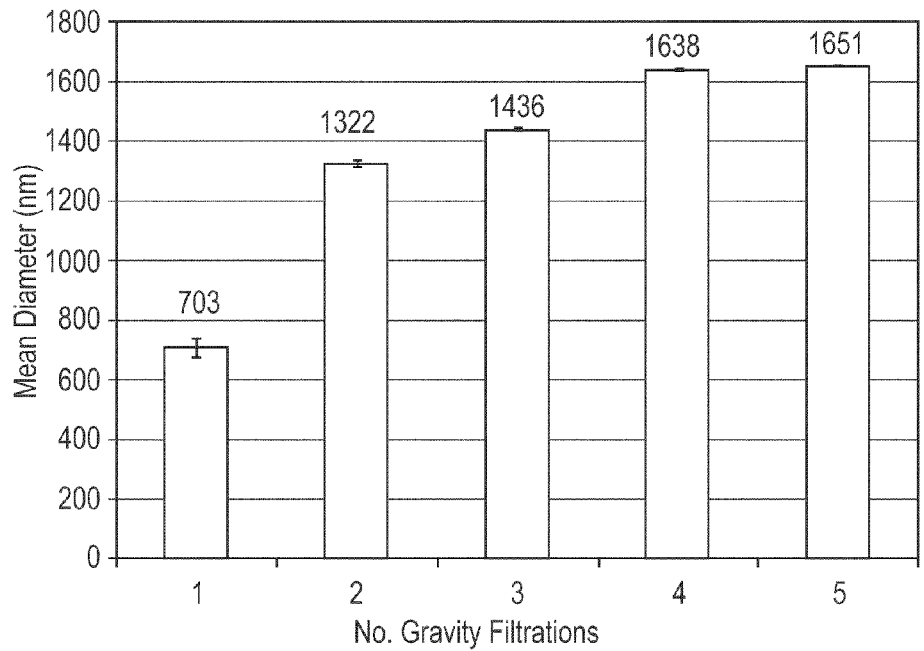
FIG. 7a shows retentate mean diameter measurements of MSN fractionation using gravity filtration, in accordance with an embodiment of the invention.

FIG. 6 is a schematic diagram of the analyzing step of the method for synthesizing MSN, in accordance with an embodiment of the invention. As further illustrated in FIG. 6, DLS may include determining the mean size of particles found in the MSN suspension using a light scatting instrument, for example, a Photocor-FC light scatting instrument equipped with a 5.0 mW laser light source at 633 nm (step 121). The scattering angle of the instrument may be set at 90°, and the measurements may be taken at 25° C. The intensity auto-correlation function yielding hydrodynamic size of the particles may be analyzed using correlation software, for example, Photocor correlation software (step 122). FIG. 7a shows retentate mean diameter measurements of MSN fractionation using gravity filtration, in accordance with an embodiment of the invention. Table 1 shows the mean diameter measurements illustrated in FIG. 7a.

TABLE 1

| No. Gravity Filtrations | Mean Diameter (nm) | Std. Dev. (nm) |
| --- | --- | --- |
| 1 | 703.42 | 65.62 |
| 2 | 1322.31 | 19.20 |
| 3 | 1436.02 | 10.34 |
| 4 | 1638.30 | 13.50 |
| 5 | 1651.10 | 12.17 |

Figure 7B:
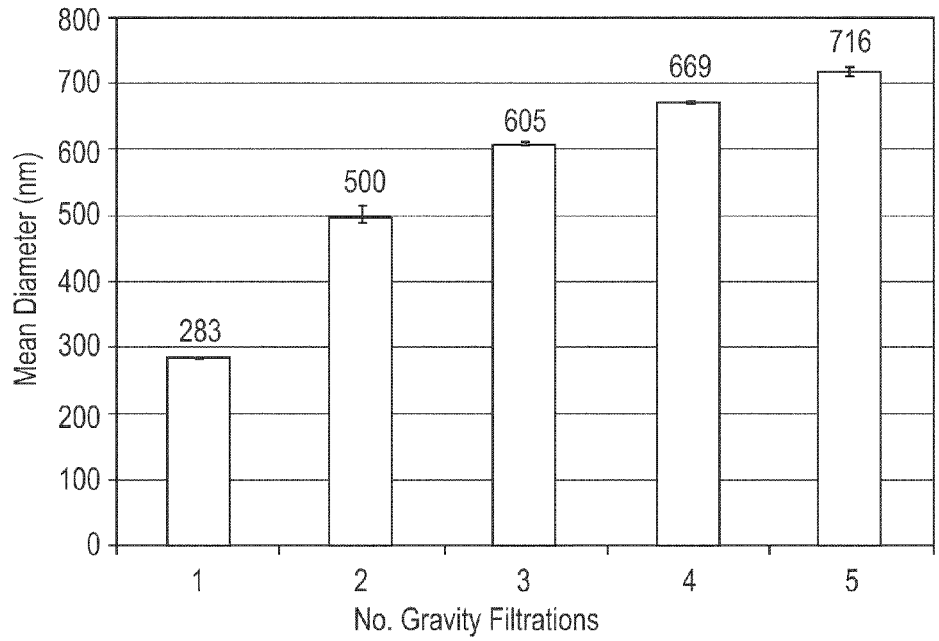
FIG. 7b shows supernatant mean diameter measurements of MSN fractionation using gravity filtration, in accordance with an embodiment of the invention.

FIG. 7b shows supernatant mean diameter measurements of MSN fractionation using gravity filtration, in accordance with an embodiment of the invention. Table 2 shows the mean diameter measurements illustrated in FIG. 7b.

TABLE 2

| No. Gravity Filtrations | Mean Diameter (nm) | Std. Dev. (nm) |
|---|---|---|
| 1 | 283.38 | 6.513 |
| 2 | 500.0 | 22.15 |
| 3 | 605.18 | 8.781 |
| 4 | 668.95 | 4.188 |
| 5 | 716.24 | 16.96 |

Figure 7C:
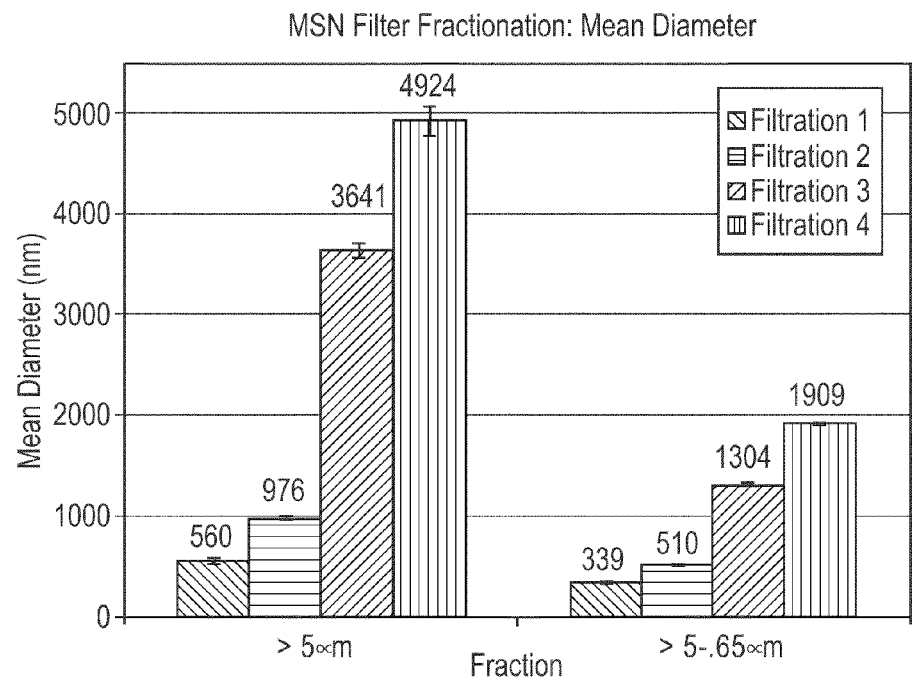
FIG. 7c shows the mean MSN diameter as measured by DLS versus the number of filtrations from MSN filter fractionation, in accordance with an embodiment of the invention.
Figure 7D:
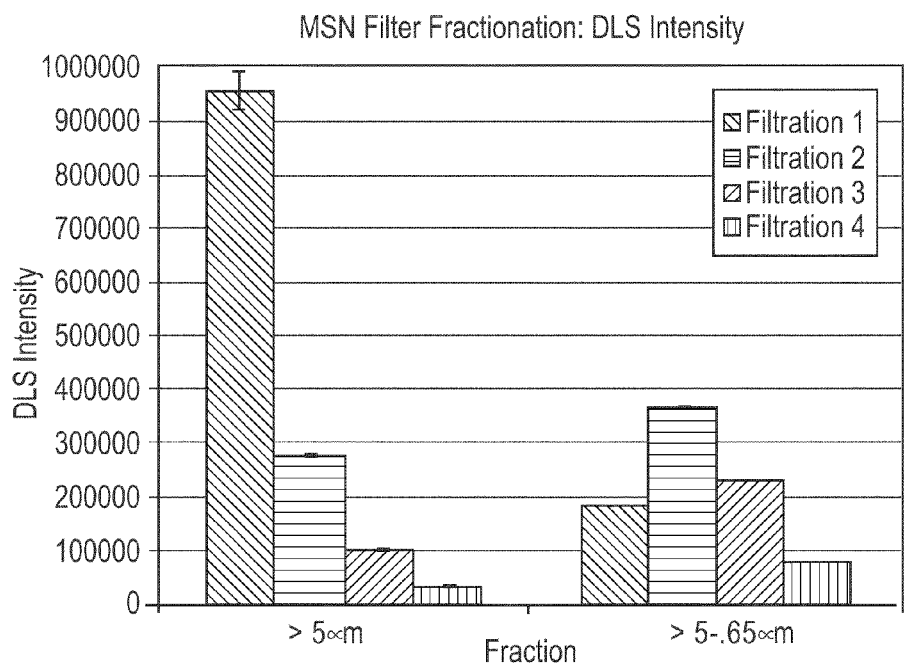
FIG. 7d shows the DLS intensity versus the number of filtrations from MSN filter fractionation, in accordance with an embodiment of the invention.

FIG. 7c shows the mean MSN diameter as measured by DLS versus the number of filtrations from MSN filter fractionation, in accordance with an embodiment of the invention. FIG. 7d shows the DLS intensity versus the number of filtrations from MSN filter fractionation, in accordance with an embodiment of the invention.

Figure 8A:
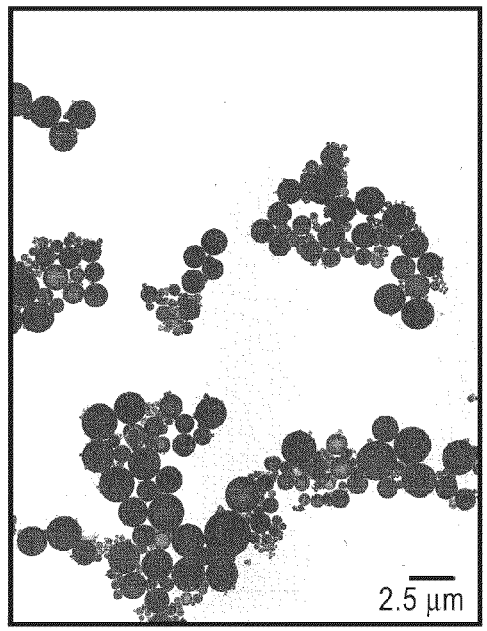
FIGS. 8a and 8b show TEM images of 5.0-0.65 μm fraction obtained by filter fractionation, in accordance with an embodiment of the invention.
Figure 8B:
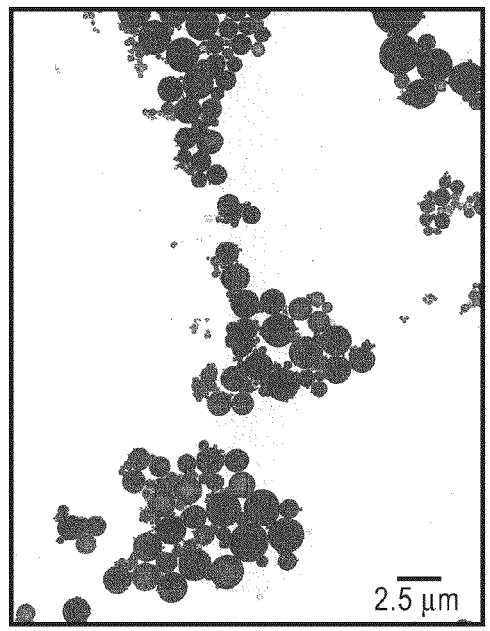
Figure 8C:
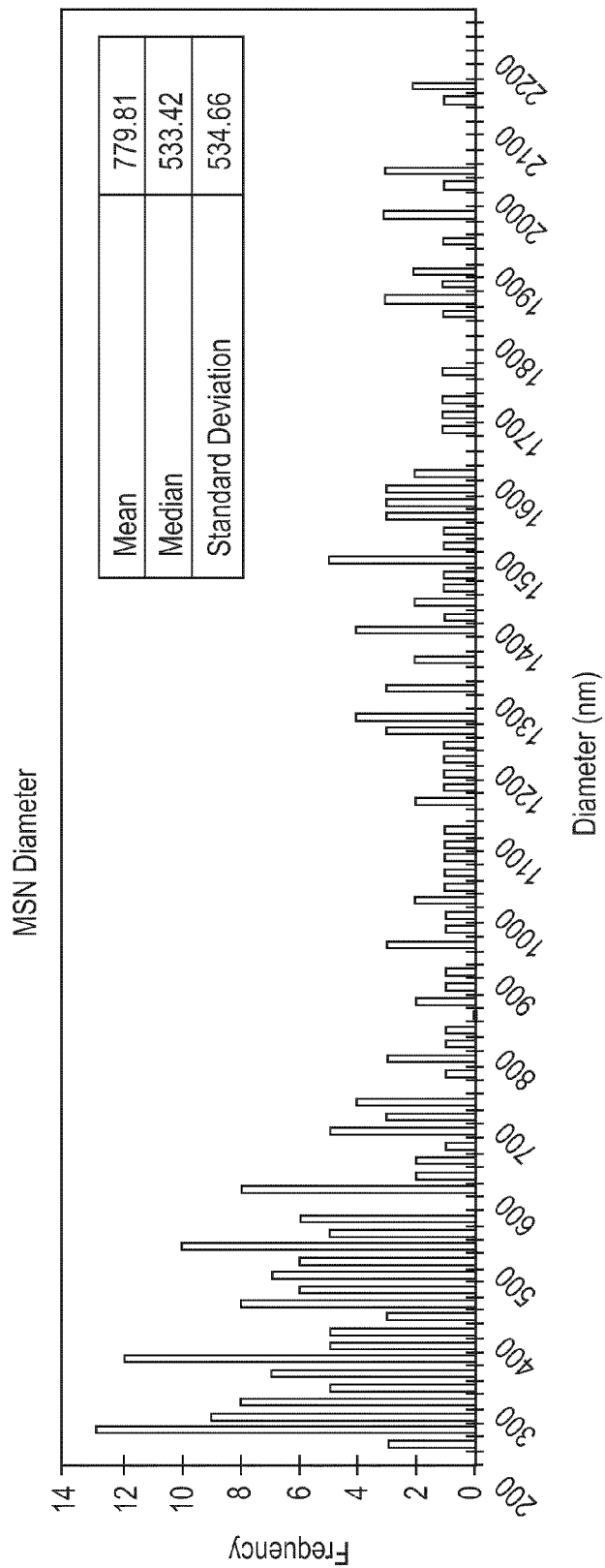
FIG. 8c is a histogram showing an ImageJ analysis of TEM image 8a, in accordance with an embodiment of the invention.
Figure 8D:
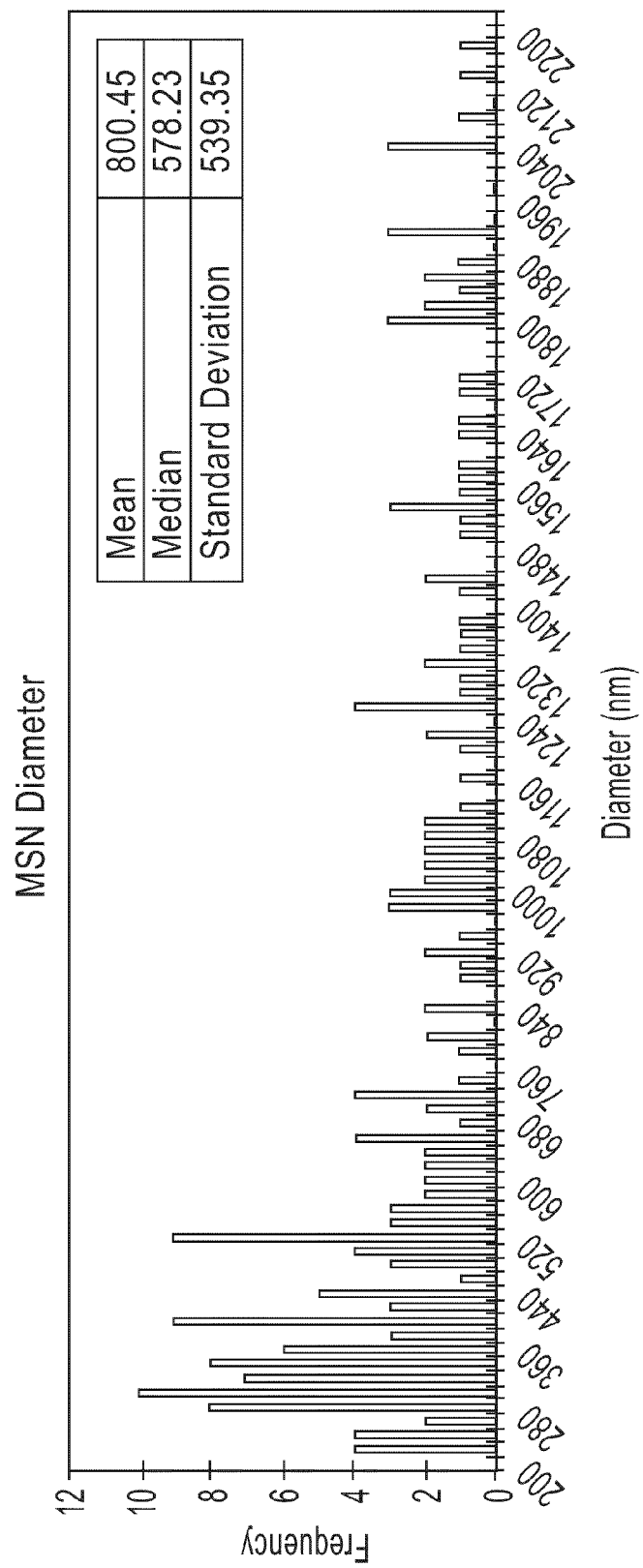
FIG. 8d is a histogram showing an ImageJ analysis of TEM image 8b, in accordance with an embodiment of the invention.
Figure 8E:
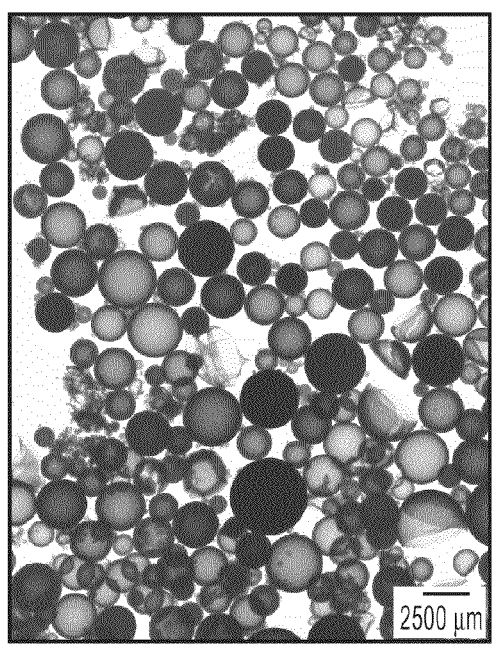
FIGS. 8e, 8f, 8g show TEM images of >5.0 μm fraction obtained by filter fractionation, in accordance with an embodiment of the invention.
Figure 8F:
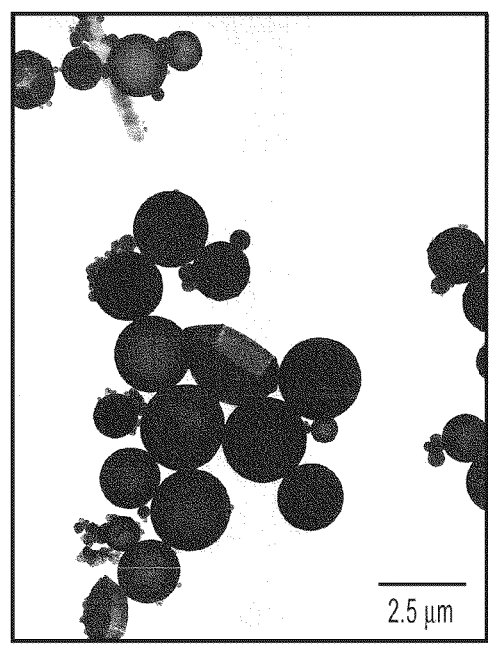
Figure 8G:
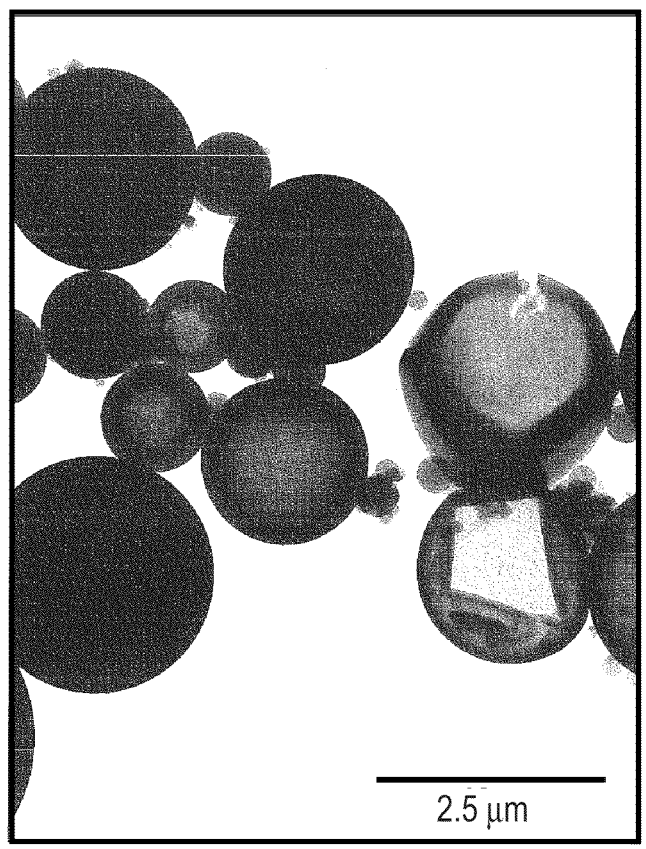
Figure 8H:
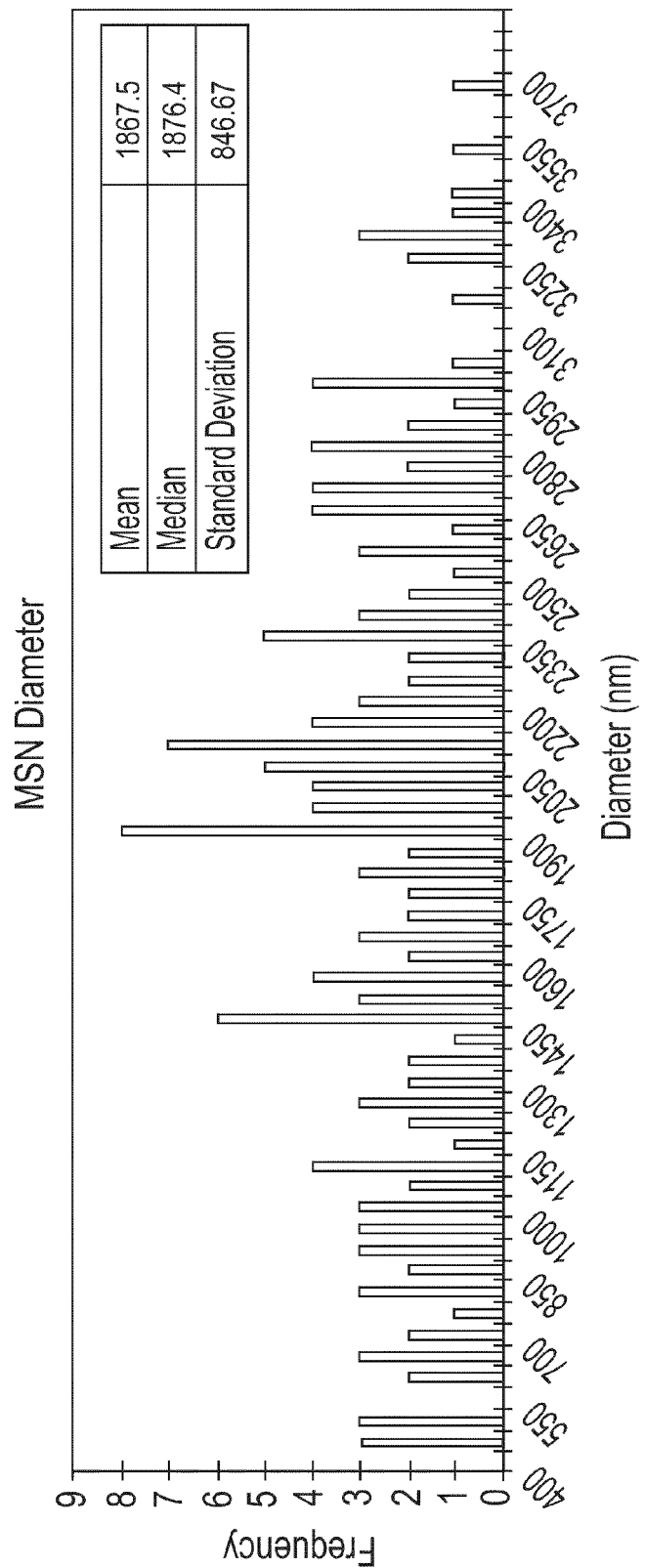
FIG. 8h is a histogram showing an ImageJ analysis of TEM image 8e, in accordance with an embodiment of the invention.

As further illustrated in FIG. 6, TEM may including preparing TEM samples by evaporating 5.0 μL of a sample in interest onto a formvar coated copper TEM grid (step 123). The sample may be allowed to evaporate for approximately five hours yielding a dry grid (step 124). The grid may be examined using a transmission emission microscope, for example, a Zeiss EM 10 CA transmission electron microscope (step 125). Images may be recorded on film and digitally scanned as a negative (step 126). MSN particle sizes may be measured using imaging software, for example, ImageJ software obtained from the National Institute of Health (step 127). FIGS. 8a and 8b show TEM images of 5.0-0.65 μm fraction obtained by filter fractionation, in accordance with an embodiment of the invention. FIG. 8c is a histogram showing an ImageJ analysis of TEM image 8a, in accordance with an embodiment of the invention. FIG. 8d is a histogram showing an ImageJ analysis of TEM image 8b, in accordance with an embodiment of the invention. FIGS. 8e, 8f, 8g show TEM images of >5.0 μm fraction obtained by filter fractionation, in accordance with an embodiment of the invention. FIG. 8h is a histogram showing an ImageJ analysis of TEM image 8e, in accordance with an embodiment of the invention.

Figure 9:
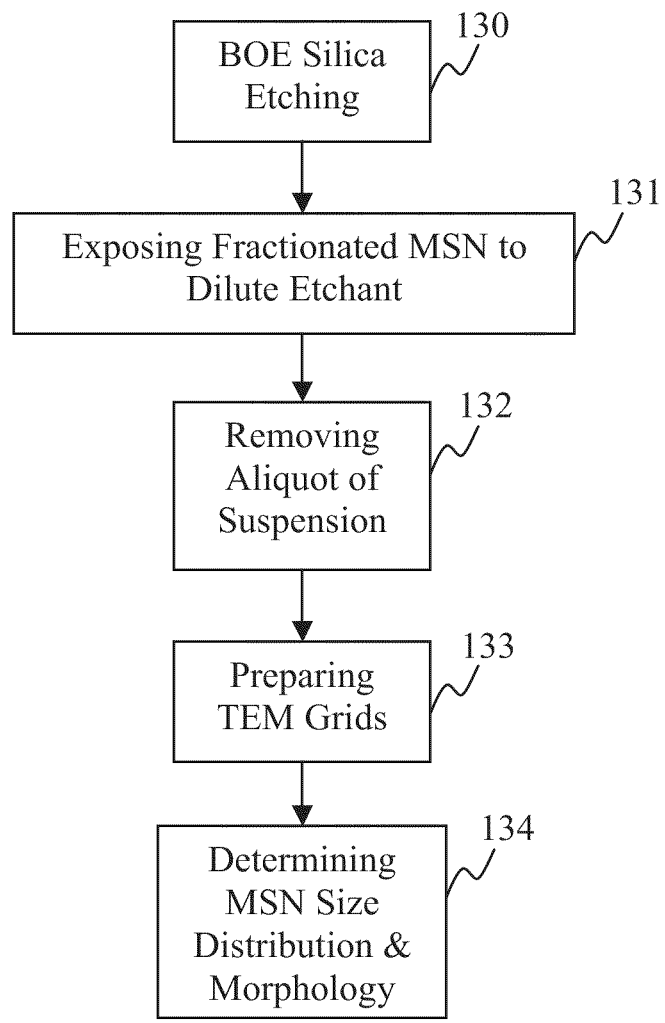
FIG. 9 is a schematic diagram of the BOE silica etching step of the method for synthesizing MSN, in accordance with an embodiment of the invention.

As illustrated in FIGS. 2 and 9, the method may further include a time-dependent water-based differential etching and re-deposition of the silica matrix from which particles are synthesized, for example, buffered oxide etchant BOE silica etching (step 130).

FIG. 9 is a schematic diagram of the BOE silica etching step of the method for synthesizing MSN, in accordance with an embodiment of the invention. BOE silica etching may include exposing the size-fractionated particles in a water suspension to a dilute etchant, for example, a BOE (step 131). An aliquot of the suspension may be removed at various time intervals, whereby the etchant may be removed by washing the suspension with water through centrifugal filtration, as previously described above (step 132). BOE silica etching may further include preparing TEM grids using collected samples of the filtrated suspension (step 133). DLS and TEM may be used to determine MSN size distribution and morphology, as previously described above (step 134). FIGS. 10a, 10b, and 10c show TEM images of MSN in a water suspension for two days, four days, and eleven days, respectively, in accordance with an embodiment of the invention.

Further experimentation may demonstrate that both sequential filter filtration and BOE silica etching may be important for the morphological changes observed in MSN. Studies indicated the gradual development of hollow morphology with increased exposure to mechanical stress through centrifugal filtration with the formation of hollow particles observed after four filtration sequences. Furthermore, although morphological changes due to time-dependent water-based etching may not be as prevalent as the gradual development of hollow morphology experienced through centrifugal filtration, water-based etching may still be essential in this process due to observations indicating a lack of hollow particle development without sufficient time exposure to water. Therefore, without proper exposure to water the silica matrix may not be chemically degraded to the point where mechanical-stress-induced morphology development can occur.

Figure 11C:
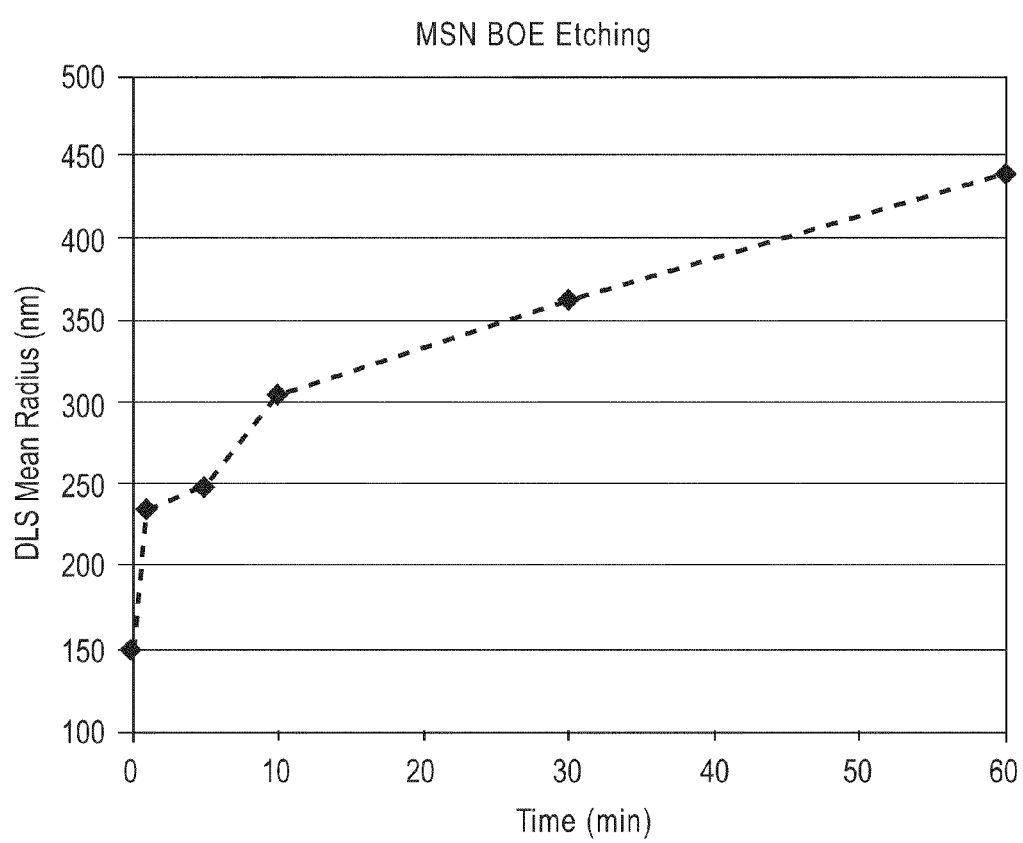
FIG. 11c is a plot of MSN radius as measured using DLS versus time exposure to BOE, in accordance with an embodiment of the invention.

Accordingly, in studies utilizing BOE silica etching techniques, the development of hollow particles may be observed over time, upon exposure to the BOE. The data collected also may indicate a corresponding increase in MSN radius with time exposure to BOE as measured using DLS. These results may indicate that hollow particle synthesis using BOE silica etching may be due to differential etching, where silica is etched from low density regions located in the center of the particles and re-deposited on more stable, densely cross-linked regions close to the particle surface. This re-deposition process may explain the corresponding increase in particle diameter with time exposure to BOE, as illustrated in FIGS. 11a, 11b, and 11c. FIGS. 11a and 11b show TEM images of hollow particles synthesized using BOE silica etching for 30 minutes, in accordance with an embodiment of the invention. FIG. 11c is a plot of MSN radius as measured using DLS versus time exposure to BOE, in accordance with an embodiment of the invention.

FIG. 12 is a schematic diagram of a method for loading and releasing a target material from mesoporous silica nanoparticles, in accordance with an embodiment of the invention. The method may include loading a target material into MSN (step 210). The target material may include a chemotherapeutic agent, for example, doxorubicin, or a fluorescent imaging agent, for example, Rhodamine 6G, or their equivalents. The step of loading may include suspending size-fractionated MSN in combination with the respective target materials. For example, the step of loading may include adding porous silica particles to 1.0 mM target material solution in water in a 1.0 mL target material/4.0 mg MSN ratio. The water may include Millipore water, for example, 18 MΩ water. The method may further include vortexing the particle solution and subsequently removing excess target material using a filter, for example, a 0.22 μm Ultrafree-CL centrifugal filter (step 212). The method may further include re-suspending and washing the particles with water of the same volume as was used to make the original suspension (step 214). The method may further include centrifuging the suspension to remove the water (step 216).

Confocal imaging, FRAP, and UV-Vis spectroscopy may be used to demonstrate that the target material was loaded into the MSN (step 218). Confocal imaging may include immobilizing MSN on cover-slips to allow their continual observation in solution. Immobilization may be achieved through sol-gel processing using tetraethyl orthosilicate (TEOS). The step of immobilizing may include immersing cover-slips in a 1:1:4 mixture of TEOS, 1 M HCl, and ethanol and sonicating the cover-slip mixture for 5 min. Next, confocal imaging may include rinsing the cover-slips with ethanol and then wetting them with the MSN solution. The solution may be allowed to evaporate overnight resulting in a random distribution of immobilized MSN on the glass cover-slip. Prior to imaging, a rubber spacer may be used to form an enclosed fluid cell between two cover-slips to prevent evaporation. The MSN may be immersed in the solution of interest by filling the sample chamber, in which the MSN coated cover-slip forms the bottom surface. The immersing solution may be exchanged with a micropipette by removing the upper coverslip.

Alternatively, fluorescence images and FRAP experiments may be conducted using a sample scanning confocal microscope. In addition to confocal imaging, the microscope may be switched to wide-field, epi-illumination employing a color CCD camera, for example, one of a Coolsnap CF, and Roper Scientific camera. In this mode, the sample may be quickly imaged to find individual MSN for confocal and FRAP analysis.

Figure 13:
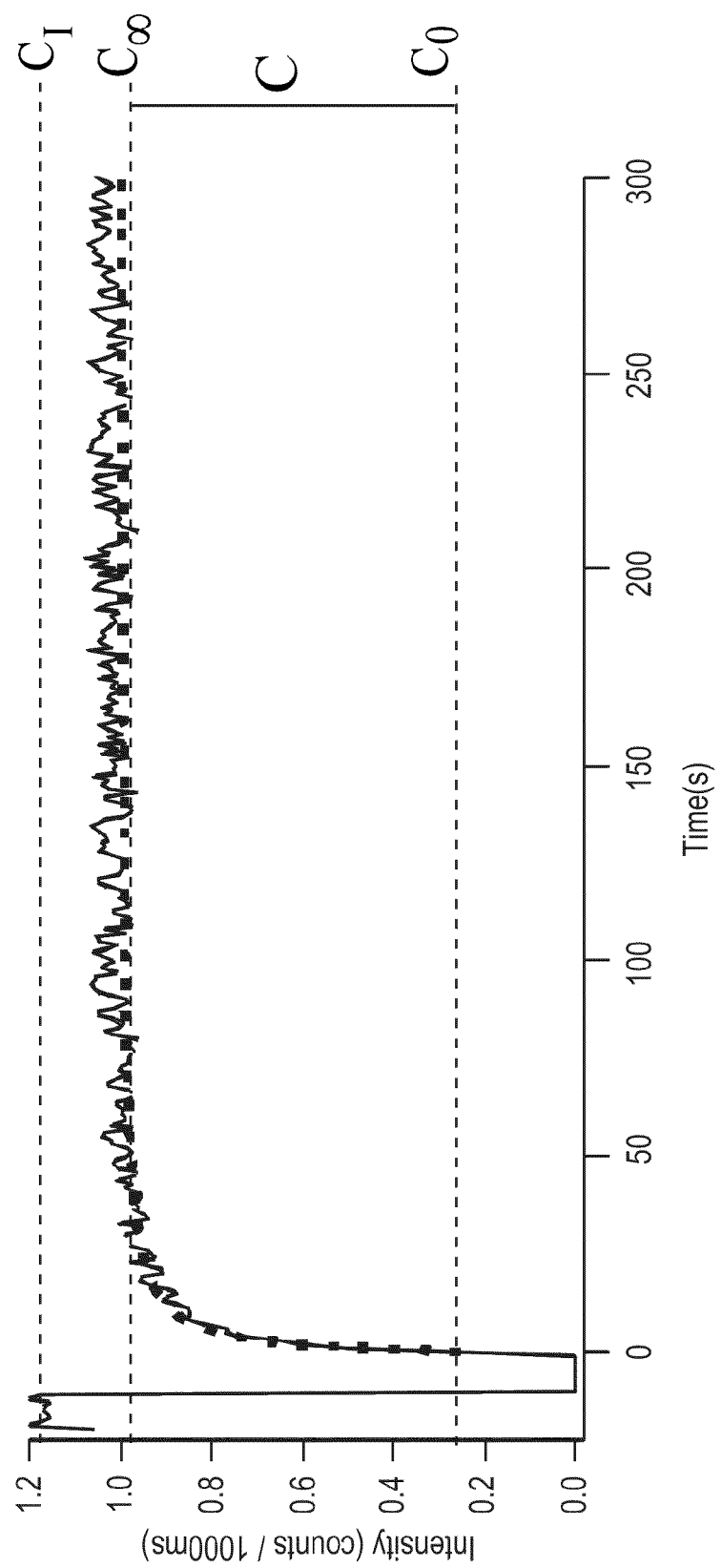
FIG. 13 shows the fluorescence recovery data for dry particles and particles immersed in phosphate buffered saline solution that has a pH of 7.4 and an ionic strength of 0.16M, in accordance with an embodiment of the invention.
Figure 14A:
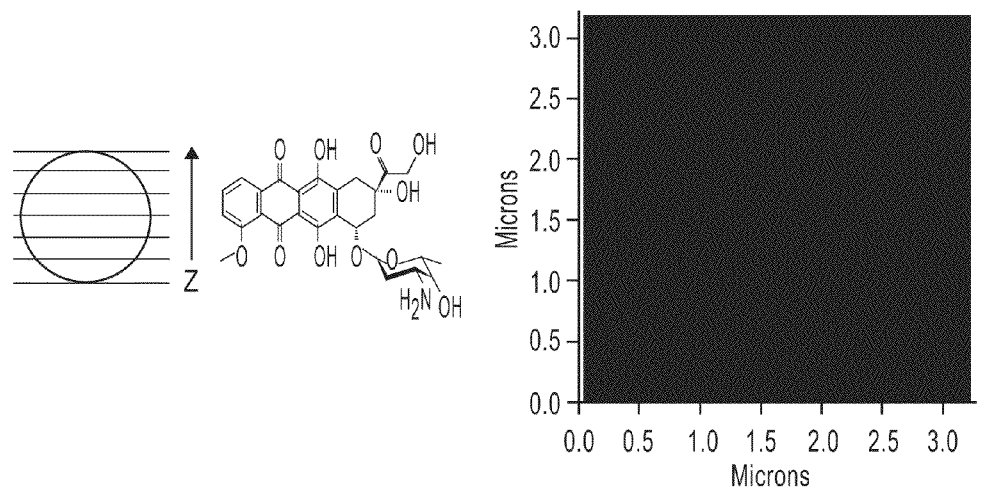
FIGS. 14a-14g show confocal images of doxorubicin loaded MSN (z=0-6 um), in accordance with an embodiment of the invention.
Figure 14B:
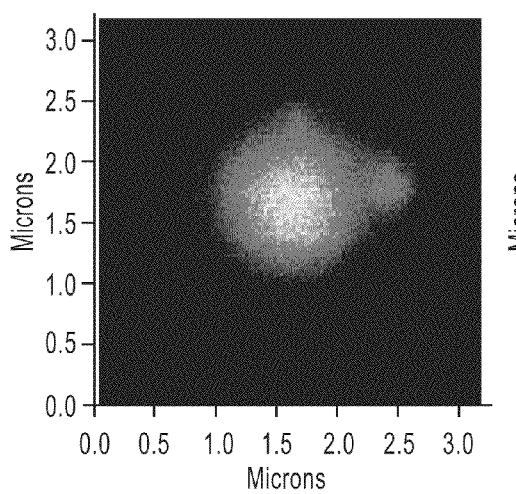
Figure 14C:
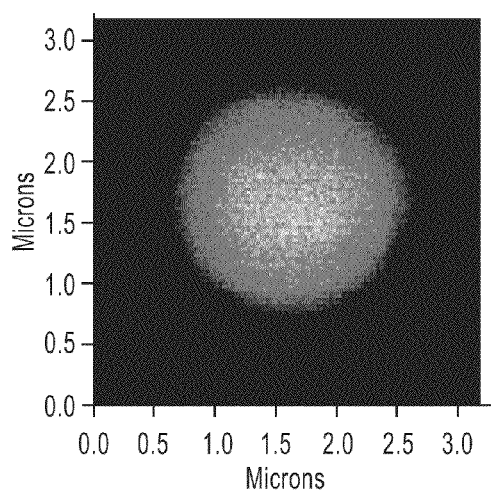
Figure 14D:
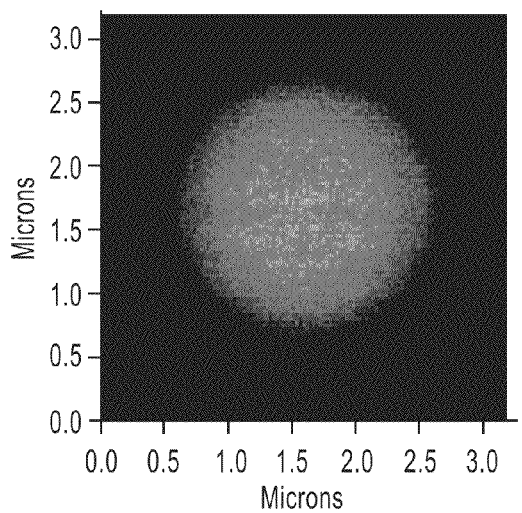
Figure 14E:
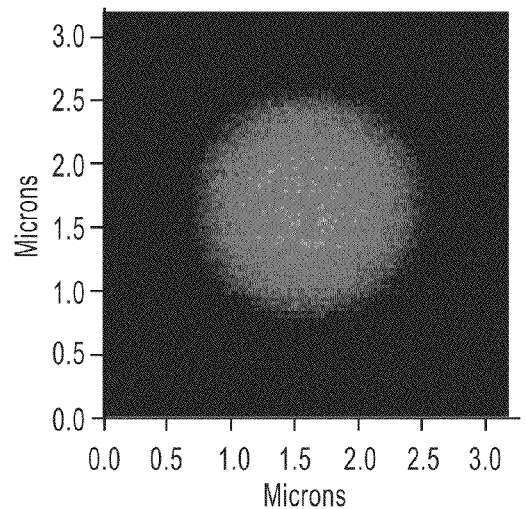
Figure 14F:
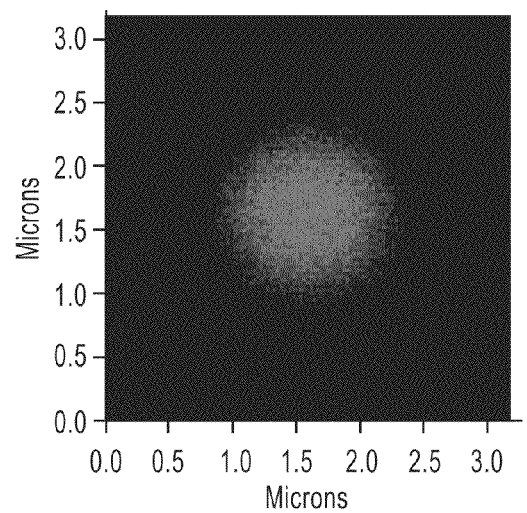
Figure 14G:
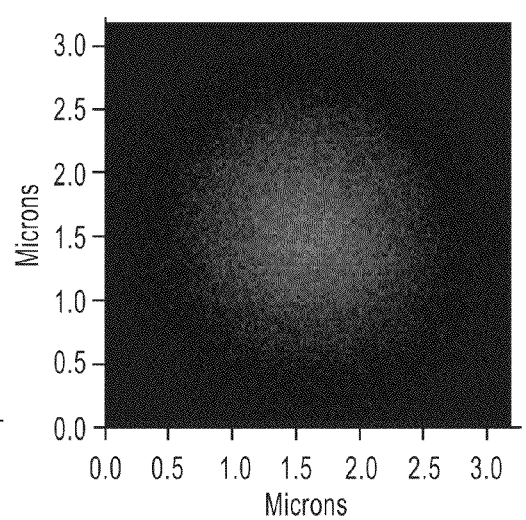

Alternatively, FRAP experiments may be conducted to demonstrate that the target material was loaded into the MSN. FRAP experiments may include bleaching the center of the doxorubicin/Rhodamine 6G-loaded MSN for 30 seconds using a focused laser spot with a total integrated power of 4 iW. After bleaching, the laser intensity may be decreased by four orders of magnitude, and a series of images may be acquired to monitor the recovery of fluorescence in each of the bleached spots. FIG. 13 shows the fluorescence recovery data for dry particles and particles immersed in phosphate buffered saline (PBS) solution that has a pH of 7.4 and an ionic strength of 0.16M, in accordance with an embodiment of the invention. $C_I$ is the initial intensity of the fluorescence of doxorubicin-HCl before photobleaching, $C_O$ is the intensity right after photobleaching, $C_\infty$ is the intensity of recovered fluorescence, and C is the bleach depth. The 'amount of recovery' can be found using the ratio $C_\infty/C_I$. The purpose of using this specific type of PBS is to mimic the conditions of blood.

After normalizing the FRAP data, the FRAP data may be fitted to the following equation:

$$C(\vec{r}, t) \propto 1 - C\left(1 + \frac{4Dt}{\rho_0^2}\right)^{-1}\left(1 + \frac{4Dt}{z_0^2}\right)^{-1/2}$$

where C(r,t) is the intensity of the fluorescence at position, r, and time, t. C is the bleach depth, D is the diffusion coefficient, $\rho_0$ and $z_0$ are pre-measured parameters, where $\rho_0$ is (1/e)*radii in the x-y plane of the bleach spot, and $z_0$ is (1/e), the distance along the coordinate of the z-axis of the bleach spot. For example, for doxorubicin, $\rho_0$ is 1.099 μm and $z_0$ may be 5.729 μm. Because $\rho_0$ and $z_0$ define the volume of the bleach spot, they may also define the position, r, in C(r,t). This function describes fluorescence recovery due to surface diffusion with the assumption of illumination by a one-dimensional Gaussian beam.

Tables 1-3, provided below, give averaged values of the parameters calculated by Equation 1, the average particle size, and the average ratio of $C_\infty/C_I$ for alumina particles and silica/gold particles, in accordance with an embodiment of the invention. The sample size may be ten particles.

TABLE 1

Averaged parameter values from 10 alumina particles

|  | Dry Particles | Particles Immersed in PBS solution PBS pH = 7.4, PBS Ionic Strength = 0.16M |
|---|---|---|
| Particle Size (μm) | 2.04 ± 0.85 | 1.70 ± 1.12 |
| C | 0.1672 ± 0.0388 | 0.4016 ± 0.1765 |
| D (cm²/s) | 2.04e−10 ± 1.69e−10 | 3.05e−10 ± 2.07e−10 |
| $C_\infty/C_I$ | 0.5440 ± 0.0838* | 0.5037 ± 0.1553 |

*Average of $C_\infty/C_0$ only counts 9 particles because 1 particle had a $C_\infty/C_0$ value >1

TABLE 2

Averaged parameter values from 10 silica/gold particles

|  | Dry Particles | Particles Immersed in PBS solution PBS pH = 7.4, PBS Ionic Strength = 0.16M |
|---|---|---|
| Particle Size (μm) | 1.22 ± 0.29 | 1.29 ± 0.56 |
| C | 0.1839 ± 0.0417 | 0.5479 ± 0.1330 |
| D (cm²/s) | 1.78e−10 ± 1.08e−10 | 1.65e−8 ± 4.63e−8 |
| $C_\infty/C_I$ | 0.7454 ± 0.1090 | 0.6508 ± 0.0985 |

TABLE 3

Averaged parameter values from 10 particle comparing alumina particles in PBS with silica/gold particles in PBS.

|  | Alumina Particles | Silica/Gold Particles |
|---|---|---|
| Particle Size (μm) | 1.70 ± 1.12 | 1.29 ± 0.56 |
| C | 0.4016 ± 0.1765 | 0.5479 ± 0.1330 |
| D (cm²/s) | 3.05e−10 ± 2.07e−10 | 1.65e−8 ± 4.63e−8 |
| $C_\infty/C_I$ | 0.5037 ± 0.1553 | 0.6508 ± 0.0985 |

PBS pH = 7.4, PBS Ionic Strength = 0.16M

Alternatively, a Beer's law standard curve, relating concentration of the target material (mg/mL) to UV-Vis absorbance for the target materials, may be constructed at the loading pH, temperature, and ionic strength conditions to demonstrate that the target material was loaded into the MSN. Absorbance spectral measurements may be taken for the target material solution before the addition of MSN. After target material is loaded into the MSN, UV-Vis spectral measurements may be taken for the supernatant separated by centrifugation. Target material concentration within MSN may be obtained from the UV-Vis spectra observed before and after loading using the previously obtained standard curve.

The method may further include quantifying the amount of MSN target material released using UV-Vis spectroscopy (step 220). The step of quantifying may include suspending target-material-loaded MSN in buffer at desired conditions, for example, pH, temperature, and ionic strength. The step of quantifying may further include removing a 2 mL aliquot from the suspension and centrifuging the suspension to separate the MSN from the solution. Further, the method may include analyzing the supernatant using UV-Vis spectroscopy to determine the concentration of target material in solution. The supernatant may be returned to the centrifuged suspension and may be subsequently vortexed to re-suspend the supernatant. The aliquot may then be returned to the bulk suspension. This process may be repeated every twenty minutes until concentration equilibrium is observed.

The uptake of doxorubicin and Rhodamine 6G into MSN may be observed to be approximately 3 ug/mg MSN as measured by UV-Vis spectroscopy. The loading of particles with doxorubicin was observed, using fluorescent confocal microscopy. FIGS. 14a-14g show confocal images of doxorubicin loaded MSN (z=0-6 um), in accordance with an embodiment of the invention. FIGS. 14a-14g show that the loading of MSN may exhibit significant fluorescence and visible emissions. Furthermore, from the obtained images, FRAP studies, and further UV-Vis spectroscopic studies quantifying target material release, it may be shown that target materials are both adsorbed onto the particle surface and contained as a freely dispersed solution within the porous bulk of the MSN. For example, MSN may be shown to retain fluorescence and visual emission signals after repeated washing using both gravity and centrifugal filtration. Therefore, it may be assumed that a significant amount of target material remains adsorbed onto the MSN surface indefinitely. This finding may indicate the potential for these materials to be effective in imaging applications where fluorescent or visual signals should remain associated with specifically targeted particles.

Figure 15A:
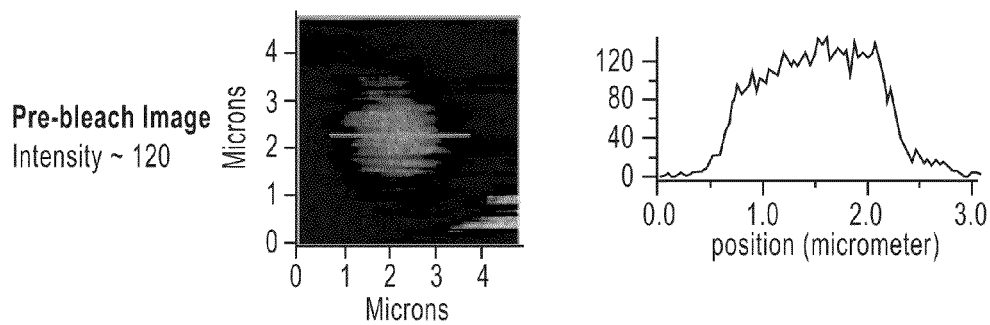
FIGS. 15a-15c show FRAP images of doxorubicin-loaded MSN before and after photo-bleaching, in accordance with an embodiment of the invention.
Figure 15B:
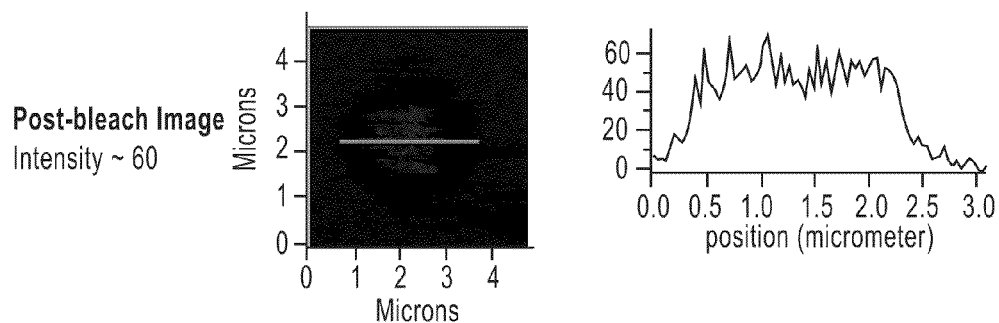
Figure 15C:
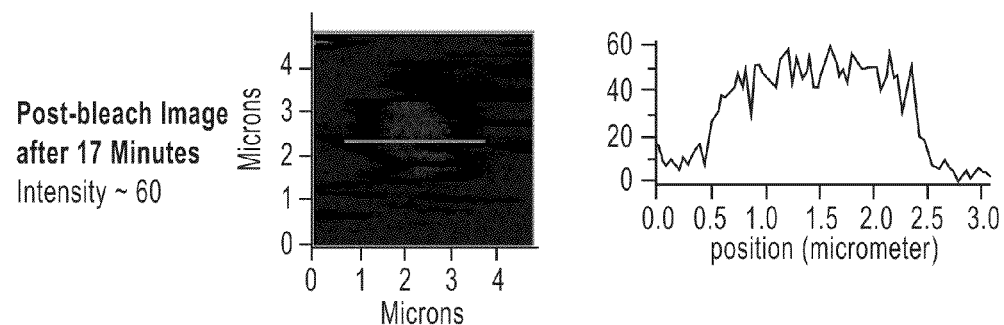
Figure 16:
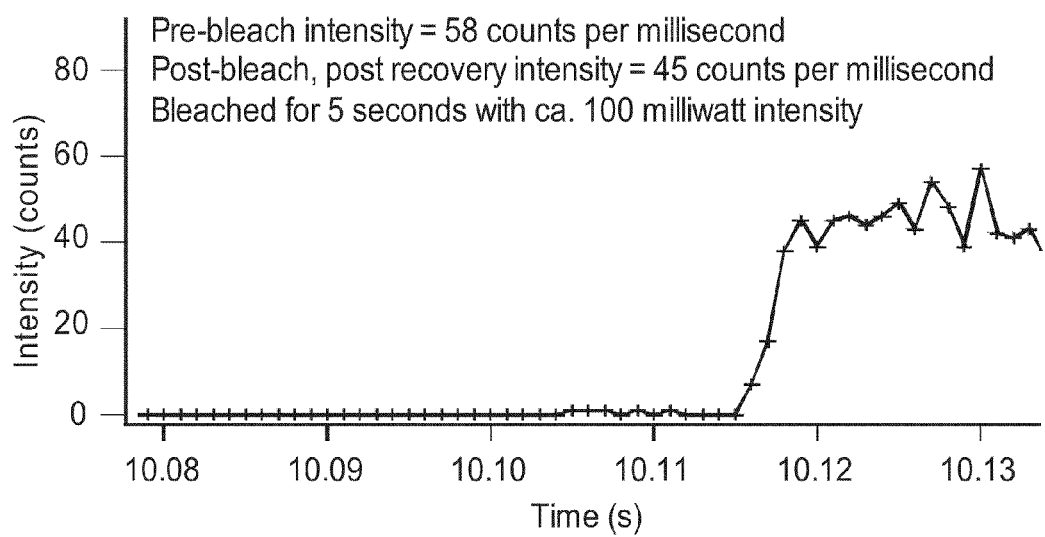
FIG. 16 is a FRAP profile for doxorubicin-loaded MSN after 5 s photo-bleaching, in accordance with an embodiment of the invention.

FIGS. 15*a*-15*c* show FRAP images of doxorubicin-loaded MSN before and after photo-bleaching, in accordance with an embodiment of the invention. FIG. 16 is a FRAP profile for doxorubicin-loaded MSN after 5 s photo-bleaching, in accordance with an embodiment of the invention. As illustrated in FIGS. 15*a*-15*c* and 16, in FRAP studies, doxorubicin loaded MSN may be found to display bulk speed fluorescence recovery with full recovery after photo-bleaching on the order of 11 ms. This observation may indicate that doxorubicin contained inside the particle is freely dispersive, thus producing the high speed fluorescence recovery profile observed. This rapid diffusion within the MSN may further demonstrate the highly porous morphology of the particles being studied and may provide evidence that porous/hollow MSN should be highly effective in transferring target materials to targeted tissues. FRAP studies have also found that, following bleaching, the decrease in fluorescence signal in doxorubicin-loaded MSN in suspension is insignificant over a time period of seventeen minutes. This indicates that, given the bleaching of, or similarly, the release of target material contained in the porous bulk, only minor target material release is observed over this time period.

This, target materials may be retained within the MSN even after washing by gravity and centrifugal filtration. This is due to the significant amount of target material that is apparently irreversibly adsorbed onto the particle surface.

The subsequent release of doxorubicin and Rhodamine 6G from MSN may be monitored under various conditions intended to mimic relevant physiological conditions using UV-Vis spectroscopy. The results obtained may indicate that release of target materials from MSN show a common exponential release profile over time. This is as predicted by Fick's law, which states that the rate of diffusion is proportional to the diffusivity of the diffusing material and the local concentration of the diffusing material. Therefore, initially when concentration of the target material inside the MSN is large, diffusion may be relatively rapid, and as the concentration is depleted due to diffusion over time, the rate of diffusion may decrease exponentially until it reaches equilibrium.

Figure 17A:
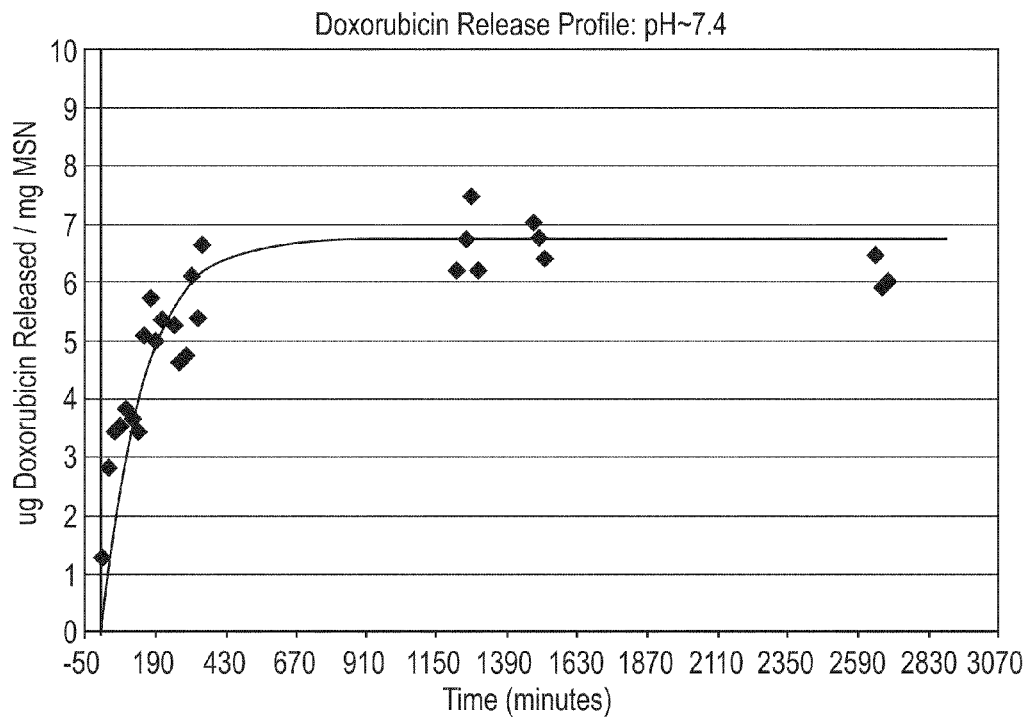
FIGS. 17a and 17b show doxorubicin release profile at pH 7.4 and pH 5.0, respectively, in accordance with an embodiment of the invention.
Figure 17B:
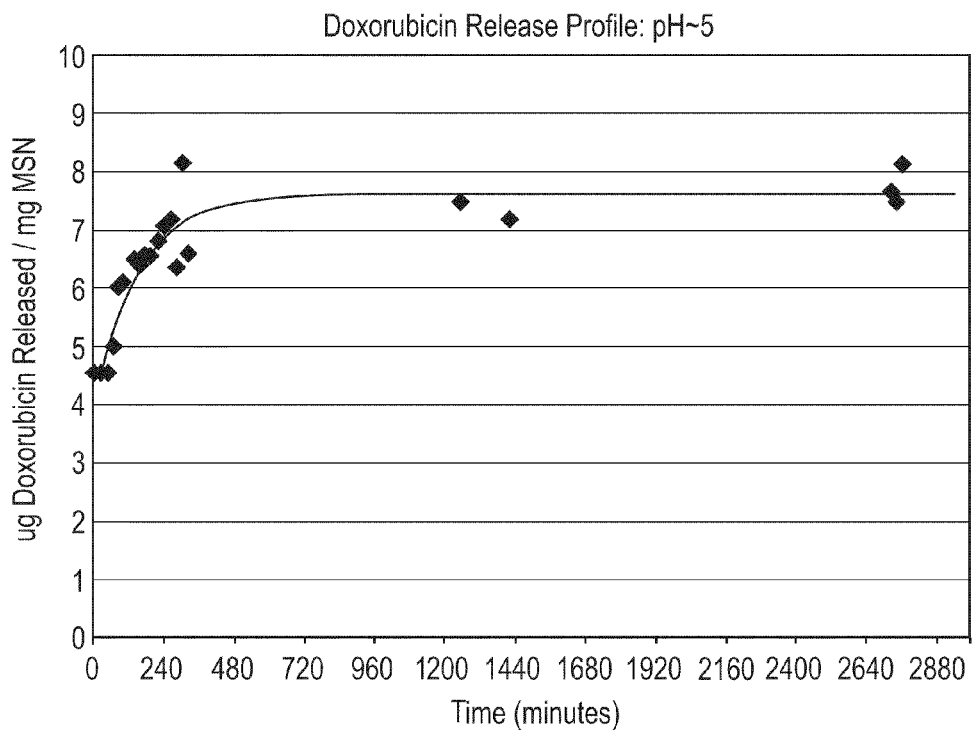

FIGS. 17*a* and 17*b* show doxorubicin release profile at pH 7.4 and pH 5.0, respectively, in accordance with an embodiment of the invention. Both profiles have I =0.137M and conducted at 25° C. as measured using UV-Vis spectroscopy at 491 nm. In the case of doxorubicin-loaded MSN, the release half life at 25° C., physiological pH (7.4), and ionic strength (I=0.137 M) was found to be approximately fifty minutes with 6 ug of doxorubicin being released per mg of MSN. Under identical conditions, a similar profile was obtained after baseline adjustment for release of Rhodamine 6G, with the release half life being approximately 30 minutes and about 6 ug of Rhodamine 6G being released per mg of MSN. This is specifically significant because this release half life may be on the order of the time typically found necessary for efficient delivery of targeted materials. Thus, the observed release time frame may provide the opportunity for targeted delivery and subsequent release needed for effective drug delivery.

The release of doxorubicin and Rhodamine 6G may also be characterized with a subsequent pH decrease to approximately pH 5.0 using hydrochloric acid. This was intended to mimic the conditions typically found in the cellular endosome, an organelle active in trafficking materials absorbed from outside the cell. In the case of doxorubicin, additional release may be measured with a release half life of approximately 50 minutes and about 7.5 ug of doxorubicin released per mg of MSN at equilibrium. In the case of Rhodamine 6G, no further release was measured with a similar decrease in pH. The modified release of doxorubicin with decreased pH may be due to decreased electrostatic surface interactions between the anionic MSN and the cationic doxorubicin. More specifically, at decreased acidic pH, i.e., pH 5.0 as compared to pH 7.4, the degree of protonation in the silanol matrix (pKa~4) may be higher, and therefore, decreased electrostatic surface interactions may be expected between the neutral, protonated silanol surface groups and positively charged doxorubicin (pKa~7).

Therefore, the additional release of doxorubicin may be attributed to decreased electrostatic interactions between the doxorubicin or the positively charged Rhodamine 6G molecules and the MSN surface at pH 5.0. This result may be specifically relevant for drug delivery as it indicates that upon MSN incorporation into the cellular endosome, the accompanying decrease in pH may stimulate release of target material. This may essentially serve as a physiologically stimulated release mechanism in targeted MSN, increasing the effectiveness of a potential drug delivery system.

Figure 18:
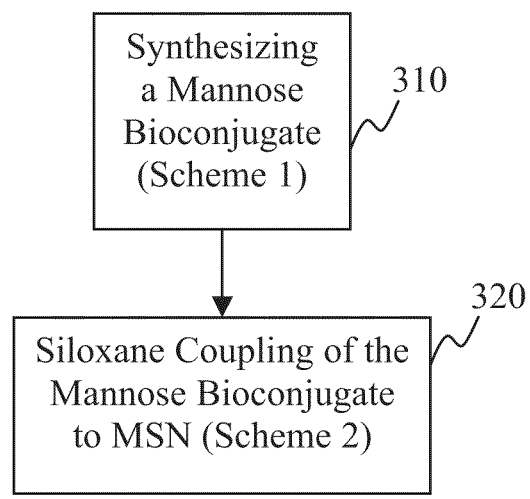
FIG. 18 is a schematic diagram of a method for functionalizing MSN with biologically relevant glycoconjugates, in accordance with an embodiment of the invention.

FIG. 18 is a schematic diagram of a method for functionalizing MSN with biologically relevant glycoconjugates, in accordance with an embodiment of the invention. Certain embodiments of the invention show that functionalizing MSN enhances MSN's ability for specific cellular targeting and facilitate the use of MSN for both specific cellular imaging and diagnostics, and targeted drug delivery. The functionalization of doxorubicin-loaded MSN may be achieved using the siloxane coupling method shown in Schemes 1 and 2. In particular, the method may include synthesis of a mannose bioconjugate using the reaction process shown in Scheme 1 with an azide formation (1), followed by an amide coupling (2), and a siloxane coupling (3) (step 310).

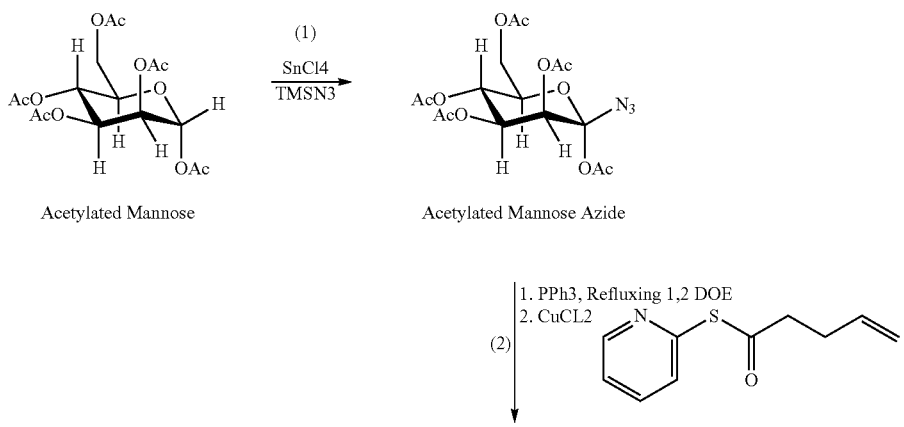

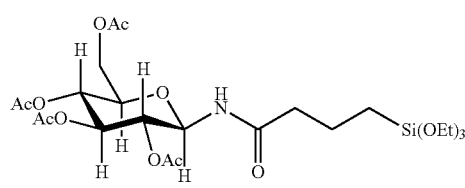

Mannose Glyco-conjugate (3) PtO2 / HSi(OEt)3

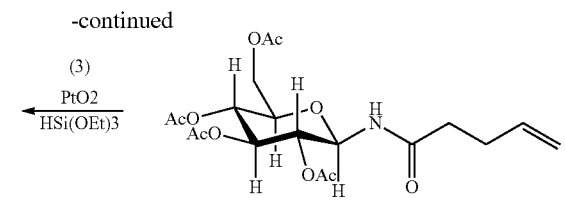

Attachment of the mannose conjugate to MSN may be accomplished according to Scheme 2 with siloxane coupling to MSN (1), followed by deacetylation (2) (step 320).

To determine the efficacy of the doxorubicin-loaded mannose-functionalized MSN, human umbilical vein endothelia cells (HUVEC) and MDA-MB 231 cells may be grown in Scheme 2

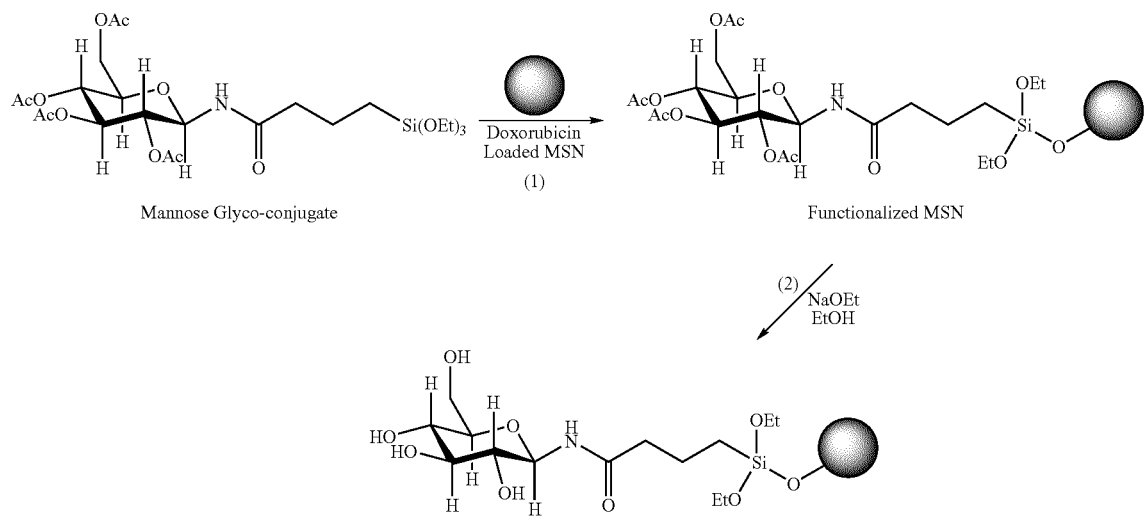

An embodiment of the invention may detect the functionalization of MSN with lactose and mannose glyco-conjugates using phenol/sulfuric acid colorimetric assay and UV-Vis spectroscopic detection of colored sugar derivatives. To confirm the effectiveness of the doxorubicin-loaded mannose-functionalized MSN, mannose-functionalized MSN samples may be incubated with type II human cancer associated macrophages. These specific cancer cells are known to have mannose receptors on their surface, and the resulting fluorescent image may indicate the specific binding of mannose-functionalized MSN.

In particular, MSN Type II cancer-associated human macrophages may be added to cover-slips in 100 μl bubbles for two hours to allow macrophage attachment. D10 medium may be added, and the cells may be rested for two hours. Doxorubicin-loaded mannose-functionalized MSN may be added to the cell cultures. After two hours, cells may be washed with phosphate buffer solution (PBS) and cells may then be treated with a 1:1000 dilution of 1 mg of propidium iodide/ml for 2 min to stain the macrophage cells. Cover-slips may then be mounted onto slides using a immunofluorescence mounting media, for example, MOWIOL®, and imaged using fluorescence.

Figure 19A:
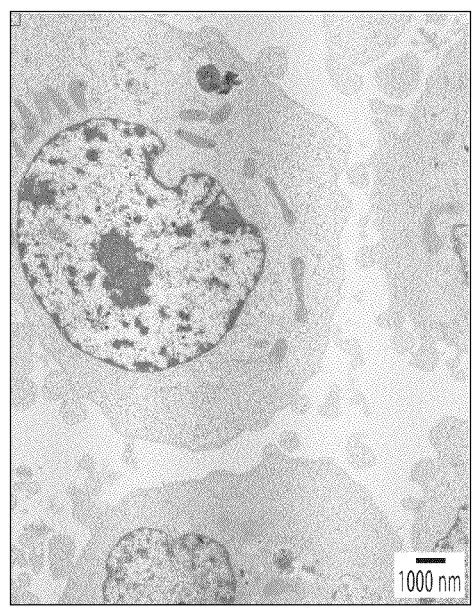
FIG. 19a is a TEM image of MDA-MB 231 human breast cancer cells incubated with MSN, in accordance with an embodiment of the invention.
Figure 19B:
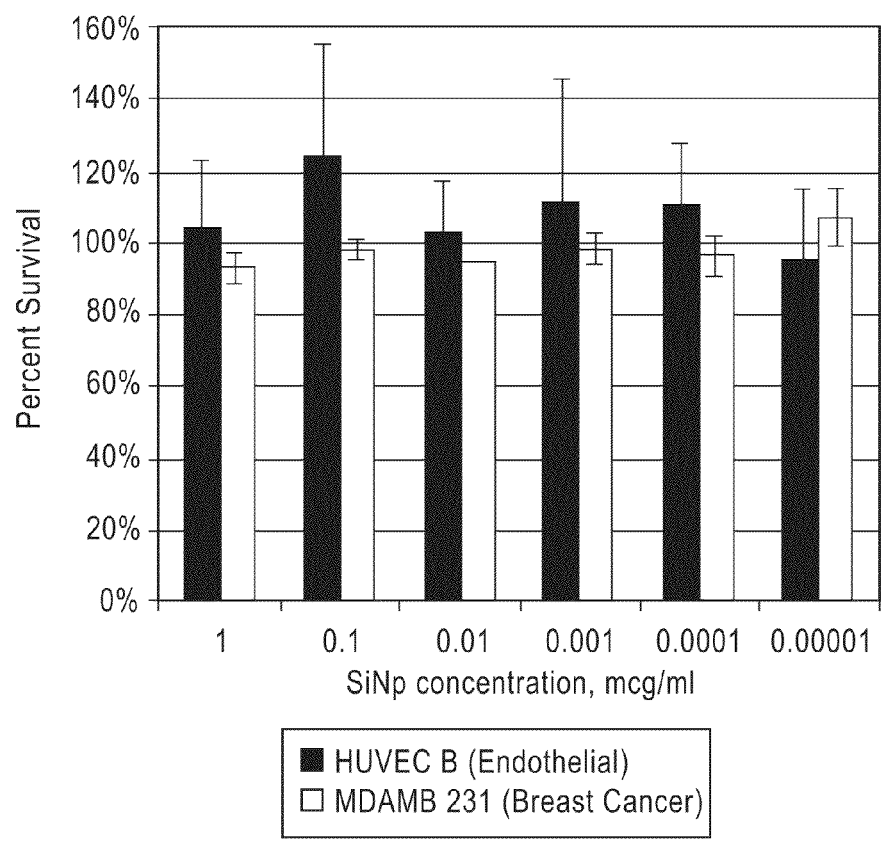
FIG. 19b is cytotoxicity data for HUVEC and MDA-MB 231 cells incubated with MSN, in vitro, in accordance with an embodiment of the invention.

Thus, MSN may be synthesized, loaded with target material, and selectively delivered to target cells. Additionally, the grouping of particles observed here may indicate that mannose receptors are displayed on the cell surface in a polarized manor with only one area.

protein-coated, 96-well, cell-assay plates providing for cell attachment and proliferation, as illustrated in FIGS. 19a and 19b. Specifically, FIG. 19a is a TEM image of MDA-MB 231 human breast cancer cells incubated with MSN, in accordance with an embodiment of the invention. FIG. 19b is cytotoxicity data for HUVEC and MDA-MB 231 cells incubated with MSN, in vitro, in accordance with an embodiment of the invention. FIG. 19b demonstrates that MSN may serve as non-cytotoxic platforms for both cellular delivery and imaging.

After one day of growth, various MSN concentrations were added to the cells growing in the wells. After three additional days, MTT was added to all wells. The resulting substrates were dissolved using dimethyl sulfoxide in all wells. Absorbance at 560 nm was measured for all wells using a UV-Vis spectrometer. Absorbance values for MSN treated wells were compared to control wells to determine % cell survival versus MSN concentration.

Figure 20:
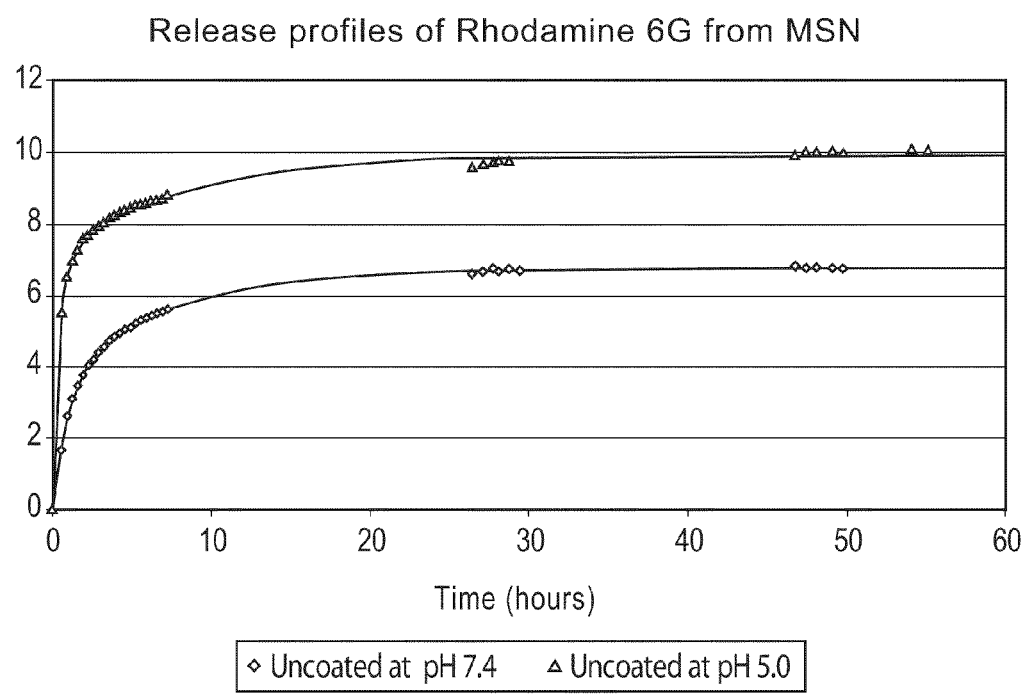
FIG. 20 is a comparison of the release of Rhodamine 6G from unmodified MSN at pH 5.0 and pH 7.4, in accordance with an embodiment of the invention.

Accordingly, certain embodiments of the invention demonstrate that MSN possess release profiles well suited for drug delivery applications with release half-lives of approximately 50 minutes, and additional stimulated release upon pH decrease from physiologically neutral pH 7.4, to acidic, endosomal pH 5.0, ensuring that the entrapped drug or imaging material would be released from the MSN only after it has been endocytosed into the target tissue, i.e., the cancer tissue. For example, the rate and amount of drug or imaging material release at pH 5.0 may be much greater than at pH 7.4 for uncoated MSN. As illustrated in FIG. 20, at pH 5.0, uncoated particles released 3 µg of Rhodamine 6G more per mg of MSN than at pH 7.4 (approximately 10.0 µg of Rhodamine 6G per mg of MSN at pH 5.0 versus approximately 7.0 µg of Rhodamine 6G per mg of MSN at pH 7.4). FIG. 20 is a comparison of the release of Rhodamine 6G from unmodified MSN at pH 5.0 and pH 7.4, in accordance with an embodiment of the invention. As noted above, the increase in rate and amount released can be attributed to decreased electrostatic interactions between the positively charged Rhodamine 6G molecules and the silica surface of the MSN at pH 5.0. The pKa of hydroxy groups on the surface of silica material is 7.0. Therefore, at pH 7.4, the surface of MSN is partially ionized, while at pH 5.0, the surface is neutral.

Figure 21:
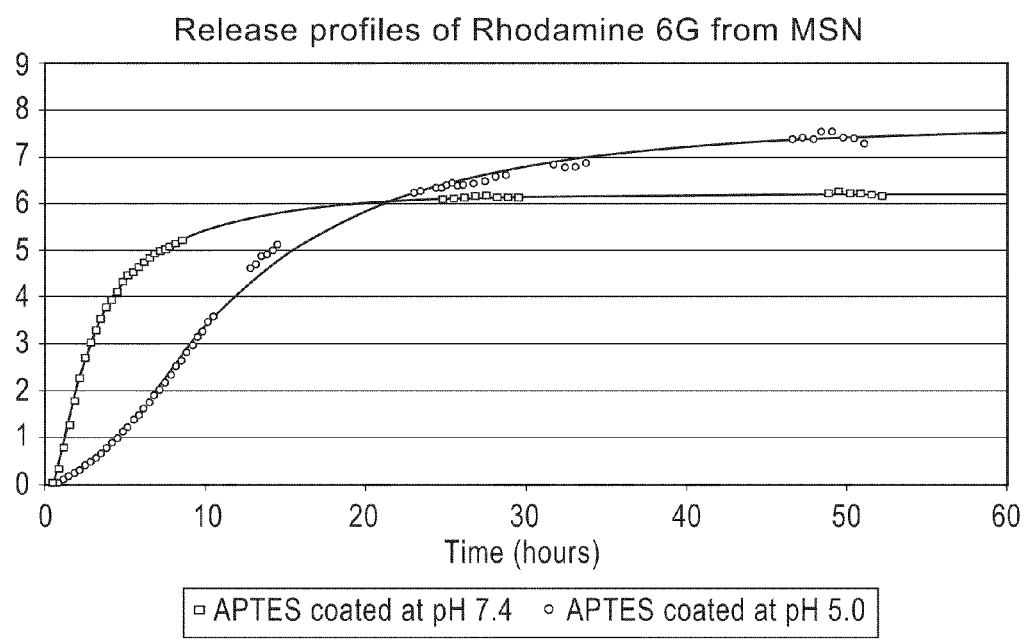
FIG. 21 is a comparison of the release profile of Rhodamine 6G from APTES-coated MSN at pH 7.4 and pH 5.0, in accordance with an embodiment of the invention.

FIG. 21 is a comparison of the release profile of Rhodamine 6G from APTES-coated MSN at pH 7.4 and pH 5.0, in accordance with an embodiment of the invention. Despite an initial lag period seen during the first hour, the release profile at pH 7.4 from the amine-coated MSN is very similar to the release profile of uncoated MSN at the same pH. Conversely, the release at pH 5.0 from the amine-coated MSN is very different than the release from any other system studied here or reported elsewhere. At pH 5.0, there is no initial burst and a longer delayed release period from the amine-coated particles. Importantly, more total release is seen at pH 5.0 than at 7.4 as with the uncoated particles, though to a lesser extent. Approximately 7.5 µg of Rhodamine 6G was released per mg of MSN at pH 5.0, while about 6.0 µg of Rhodamine 6G was released per mg of MSN at pH 7.4 (FIG. 3). The lag period at pH 7.4 and the different release profile at pH 5.0 seen for the amine-coated MSN may be rationalized by considering the surface coverage and charge of these particles. The method used to functionalize the MSN with APTES may be expected to preferentially functionalize the external surface, rather than the internal pore surface of the MSN. Such a modification may decrease the size of the pore openings, and may hinder the ability for Rhodamine 6G molecules to escape. In addition, some of the amine groups present at the surface of the MSN may be protonated at pH 7.4. Thus, for Rhodamine 6G molecules (which are positively charged under physiological conditions) to be released from these particles, they may travel through a partially positive charged coating. Under more acidic conditions, a larger number of amine groups on the surface of the particles may be protonated. The increased repulsive interaction between the positively charged amine groups and Rhodamine 6G molecules may prevent binding of Rhodamine 6G to the exterior surface of the MSN at pH 5.0. This may explain why no initial burst of release is seen at pH 5.0 for the APTES-coated MSN. The decreased dimensions of the pore openings and repulsive interaction between Rhodamine 6G and the protonated amine groups located on the surface of the MSN may be the cause of lag seen at pH 7.4, and the diminished release rate seen at pH 5.0 for these amine-coated MSN. However, FIG. 21 still shows that the rate and amount of drug or imaging material release at pH 5.0 may be much greater than at pH 7.4 for coated MSN, as was the case with uncoated MSN.

Therefore, the functionalization of the MSN, in accordance with an embodiment of the invention, may provide for a stimulated release upon pH decrease from physiologically neutral pH 7.4, to acidic, endosomal pH 5.0, ensuring that the entrapped drug or imaging material would be released from the MSN only after it has been endocytosed into the target tissue, i.e., the cancer tissue.

Furthermore, cytotoxicity studies have shown MSN, in accordance with certain embodiments of the invention, to be relatively non-cytotoxic to healthy human endothelial cells, as well as, to human breast cancer cells, making them an ideal medium for the selective delivery of drug/imaging materials. In addition, functionalization of MSN with biologically relevant glycoconjugates, in accordance with certain embodiments of the invention, has been shown to facilitate specific cellular targeting, demonstrating a proof of concept for a general approach to specific cell targeting in both specific cellular imaging and diagnostics, as well as, targeted drug delivery applications.

It is to be understood that in the embodiment of the invention, the steps are performed in the sequence and manner as shown although the order of some steps and the like may be changed without departing from the spirit and scope of the present invention. In addition, the methods described in FIGS. 2-3, 6, 9, 12, and 18 may be repeated as many times as needed.

The many features of the invention are apparent from the detailed specification and, thus, it is intended by the appended claims to cover all such features of the invention which fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

We claim:

1. A method comprising:
   providing a suspension of mesoporous silica nanoparticles, wherein the mesoporous silica nanoparticles comprise areas of low polymeric density and areas of high polymeric density;
   fractionating the mesoporous silica nanoparticles suspension to yield size-fractionated mesoporous silica nanoparticles;
   differential etching of silica from areas of low polymeric density within the size-fractionated mesoporous silica nanoparticle; and
   re-depositing the silica in areas of higher polymeric density existing near a surface of the size-fractionated mesoporous silica nanoparticles to produce mesoporous silica nanoparticles having a morphology that changes from porous to hollow and wherein said nanoparticles are configured to receive one of a therapeutic agent and an imaging material.

2. The method of claim 1, further comprising:
   analyzing the size-fractionated mesoporous silica nanoparticles to determine a mean size of the mesoporous silica nanoparticles.

3. The method of claim 2, wherein the analyzing comprises performing one of dynamic light scattering and transmission electron microscopy.

4. The method of claim 1, wherein the fractionating comprises performing one of a centrifugal filter fractionation and a gravity filter fractionation.

5. The method of claim 4, wherein the performing the centrifugal filter fractionation comprises filtering a retentate of the mesoporous silica nanoparticle suspension until the mesoporous silica nanoparticles have been filtered using five separate filters.

6. The method of claim 1, wherein the etching further comprises exposing the size-fractionated mesoporous silica nanoparticles to a buffered oxide etchant.

7. The method of claim 1, wherein the therapeutic agent is a cancer treatment drug.

8. The method of claim 7, wherein the cancer treatment drug is doxorubicin.

9. The method of claim 1, wherein the imaging agent is Rhodamine 6G.

10. The method of claim 4, further comprising:
    analyzing the size-fractionated mesoporous silica nanoparticles to determine a mean size of the mesoporous silica nanoparticles, wherein the analyzing step follows each filtration performed in the fractionating step.

11. The method of claim 10, wherein the analyzing comprises performing one of dynamic light scattering and transmission electron microscopy.

* * * * *